US010898870B2

(12) United States Patent
Hurd et al.

(10) Patent No.: US 10,898,870 B2
(45) Date of Patent: Jan. 26, 2021

(54) LIQUID MIXING SYSTEM WITH VERTICALLY ADJUSTABLE MIXING ELEMENT AND METHOD OF USE

(71) Applicant: LIFE TECHNOLOGIES CORPORATION, Carlsbad, CA (US)

(72) Inventors: Jeffery C. Hurd, Hyrum, UT (US); Nephi D. Jones, Newton, UT (US); Jacob D. Lee, Smithfield, UT (US)

(73) Assignee: Life Technologies Corporation, Carlsbad, CA (US)

( * ) Notice: Subject to any disclaimer, the term of this patent is extended or adjusted under 35 U.S.C. 154(b) by 538 days.

(21) Appl. No.: 15/799,580

(22) Filed: Oct. 31, 2017

(65) Prior Publication Data

US 2018/0117546 A1    May 3, 2018

Related U.S. Application Data

(60) Provisional application No. 62/415,949, filed on Nov. 1, 2016.

(51) Int. Cl.
*B01F 7/00* (2006.01)
*B01F 15/00* (2006.01)
(Continued)

(52) U.S. Cl.
CPC .......... *B01F 7/0095* (2013.01); *B01F 3/0412* (2013.01); *B01F 7/001* (2013.01); *B01F 7/007* (2013.01); *B01F 7/00341* (2013.01); *B01F 7/00675* (2013.01); *B01F 7/00691* (2013.01); *B01F 7/00725* (2013.01);
(Continued)

(58) Field of Classification Search
CPC ...... B01F 7/161; B01F 7/0095; B01F 7/1695; B01F 13/0018
See application file for complete search history.

(56) References Cited

U.S. PATENT DOCUMENTS 2,625,720 A * 1/1953 Ross .................... B41B 5/06
222/318
5,356,214 A   10/1994 Styles
(Continued)

FOREIGN PATENT DOCUMENTS

DE    20 2010 005709    9/2010
DE    10 2009 041569    4/2011
(Continued)

OTHER PUBLICATIONS

International Search Report and Written Opinion dated Feb. 16, 2018, issued in PCT Application No. PCT/US2017/059335, filed Oct. 31, 2017.

*Primary Examiner* — Elizabeth Insler
(74) *Attorney, Agent, or Firm* — Workman Nydegger

(57) ABSTRACT

A liquid mixing system includes a support housing at least partially bounding a compartment. A mount is secured to the support housing. A drive motor assembly is configured to engage a drive shaft for moving the drive shaft within the compartment of the support housing. A four bar linkage system extends between the mount and the drive motor assembly, the four bar linkage system being movable between a first position wherein the drive motor assembly is disposed at a first elevation and a second position wherein the drive motor assembly is disposed at a second elevation that is different from the first elevation.

18 Claims, 12 Drawing Sheets

(51) Int. Cl.
  *B01F 3/04* (2006.01)
  *C12M 1/06* (2006.01)
  *C12M 1/00* (2006.01)
  *C12M 1/34* (2006.01)

(52) U.S. Cl.
  CPC .... *B01F 15/00006* (2013.01); *B01F 15/0085* (2013.01); *C12M 23/14* (2013.01); *C12M 23/26* (2013.01); *C12M 27/02* (2013.01); *C12M 41/44* (2013.01); *B01F 2003/04191* (2013.01); *B01F 2215/0032* (2013.01); *B01F 2215/0073* (2013.01)

(56) References Cited

U.S. PATENT DOCUMENTS

| | | | |
|---|---|---|---|
| 6,083,587 A | 7/2000 | Smith et al. | |
| 6,135,630 A * | 10/2000 | O'Neill | B01F 7/1605 366/281 |
| 6,617,146 B1 | 9/2003 | Naccarato et al. | |
| 6,908,223 B2 | 6/2005 | Bibbo et al. | |
| 7,384,783 B2 | 6/2008 | Kunas et al. | |
| 7,682,067 B2 | 3/2010 | West et al. | |
| 7,879,599 B2 | 2/2011 | Goodwin et al. | |
| 8,623,640 B2 | 1/2014 | Kunas et al. | |
| 8,641,314 B2 | 2/2014 | Thacker et al. | |
| 8,960,486 B2 | 2/2015 | Goodwin et al. | |
| 2002/0131654 A1 | 9/2002 | Smith et al. | |
| 2003/0077466 A1 | 4/2003 | Smith et al. | |
| 2005/0259511 A1 * | 11/2005 | Orton | B28C 5/0893 366/285 |
| 2006/0240546 A1 | 10/2006 | Goodwin et al. | |
| 2006/0270036 A1 | 11/2006 | Goodwin et al. | |
| 2006/0280028 A1 | 12/2006 | West et al. | |
| 2008/0186802 A1 | 8/2008 | Bungay | |
| 2010/0097882 A1 | 4/2010 | Unlenkamp | |
| 2010/0149908 A1 * | 6/2010 | Singh | B01F 15/0085 366/276 |
| 2010/0159524 A1 | 6/2010 | Smith et al. | |
| 2011/0188928 A1 | 8/2011 | West et al. | |
| 2011/0310696 A1 | 12/2011 | Goodwin et al. | |
| 2012/0113741 A1 | 5/2012 | Filipitsch et al. | |
| 2013/0101982 A1 | 4/2013 | Goodwin et al. | |
| 2015/0138913 A1 | 5/2015 | Jones et al. | |
| 2016/0193576 A1 | 7/2016 | Larsen et al. | |
| 2016/0304824 A1 * | 10/2016 | Mahajan | C12M 23/52 |

FOREIGN PATENT DOCUMENTS

| | | |
|---|---|---|
| EP | 1 321 756 A1 | 6/2003 |
| EP | 1 762 607 A1 | 3/2007 |
| EP | 2 602 020 A2 | 6/2013 |
| EP | 2 689 860 A1 | 1/2014 |
| EP | 3 000 775 A1 | 3/2016 |

* cited by examiner

LIQUID MIXING SYSTEM WITH VERTICALLY ADJUSTABLE MIXING ELEMENT AND METHOD OF USE

CROSS-REFERENCE TO RELATED APPLICATIONS

This application claims the benefit of US Provisional Application No. 62/415,949, filed Nov. 1, 2016, which is incorporated herein by specific reference.

BACKGROUND OF THE INVENTION

1. The Field of the Invention

The present invention relates to liquid mixing systems that are commonly used as bioreactors or fermenters and have a vertically adjustable mixing element.

2. The Relevant Technology

The biopharmaceutical industry uses a broad range of liquid mixing systems for a variety of processes such as in the preparation of media and buffers and in the growing of cells and microorganisms. Some conventional mixing systems, including bioreactors, comprise a flexible bag disposed within a rigid support housing. An impeller is disposed within the flexible bag and is used to mix or suspend the solution within the bag. In some embodiments, the impeller is mounted to the bottom of the bag and is magnetically driven. In other embodiments, the impeller is fixed on the end of a drive shaft that projects into the flexible bag. In both embodiments, however, the impeller is designed to remain at a substantially fixed position which is optimal for mixing a narrowly defined volume of solution in the flexible bag. To enable homogeneous mixing of larger volumes of solution, larger bags are used that have an impeller positioned at a location that is optimal for that size of bag.

In some processing procedures it can be desirable to initially mix solutions at a low volume and then progressively increase the volume of the solution. For example, this is a common procedure used with bioreactors for growing cells. The process typically entails dispensing a seed inoculum in a growth media contained within a relatively small bag and then transferring the solution to progressively larger bags where additional media is added as the cells grow and multiply. This process is repeated until a final desired volume is achieved. By transferring the solution to different sized bags which each have a corresponding mixer, the operator can ensure homogeneous mixing of each of the different volumes.

Although the above process of moving solutions to different sized bags to maintain proper mixing and suspension is functional, the procedure has some shortcomings. For example, the necessity of stepping to different sized bags is labor intensive, time consuming, and has high material costs in that the multiple bags are discarded after use. Furthermore, transferring between different bags produces some mixing down-time which can influence cell growth. In addition, the necessity of shifting between bags increases the risk of contamination to the solution and potential damage to the cells.

Accordingly, what is needed in the art are improved mixing systems that solve all or some of the above problems.

SUMMARY OF THE INVENTION

In a first independent aspect of the present invention, a liquid mixing system includes:

a support housing at least partially bounding a chamber, the support housing having a top opening that communicates with the compartment;

a mount secured to the support housing so as to span across the top opening; and a drive motor assembly secured to the mount so that the drive motor assembly can be selectively raised and lowered between at least two positions, the drive motor being configured to engage a drive shaft for moving the drive shaft within the chamber of the support housing.

In one embodiment, a four bar linkage system secures the drive motor assembly to the mount, the four bar linkage system being movable to selectively raise and lower the drive motor assembly between the at least two positions.

In another embodiment, the four bar linkage system is movable between a lowered position wherein the drive motor assembly is disposed at a first angular orientation and an elevated raised position wherein the drive motor assembly is disposed at a second angular orientation that is different from the first angular orientation.

In another embodiment, the angular orientation of the drive motor assembly automatically changes as the four bar linkage system is moved between the lowered position and the raised position.

In another embodiment, the angular orientation of the drive motor assembly changes in a range between 1° and 15° and more commonly between 1° and 10°, 2° and 7°, or 2° and 5° as the four bar linkage system is moved between the lowered position and the raised position.

In another embodiment, the four bar linkage system comprises four arms each having a first end hingedly connected to the drive motor assembly and an opposing second end hingedly connected to the mount.

In another embodiment, the invention further comprises:

a support extending between two of the four arms of the four bar linkage system; and a drive assembly extending between the mount and the support.

In another embodiment, the mount comprises:

an elongated first rail spanning across the top opening and having opposing ends secured to the support housing;

an elongated second rail spanning across the top opening and having opposing ends secured to the support housing, the second rail being spaced apart from the first rail;

a brace extending between the first rail and the second rail so as to be disposed over the top opening.

In another embodiment, the first rail and the second rail are U-shaped or arched shaped and upwardly project from the support housing.

In another embodiment, a drive assembly extends between the mount and the four bar linkage system and controls movement of the four bar linkage system.

In another embodiment, the drive assembly comprises a hydraulic or pneumatic piston.

In another embodiment, the support housing has an annular flange that encircles the top opening, the mount being secured on opposing sides of the annular flange so that the mount spans entirely across the top opening.

In another embodiment, a flexible bag is disposed within the chamber of the support housing, the flexible bag bounding a compartment and being coupled to the drive motor assembly.

In another embodiment, the flexible bag is collapsible and is comprised of a polymeric film having a thickness in a range between 0.02 mm and 1 mm with between 0.02 mm and 0.5 mm and between about 0.02 and 0.2 mm being more common.

In another embodiment, a drive shaft is coupled with the drive motor assembly, at least a portion of the drive shaft being disposed within the compartment of the flexible bag, the drive motor assembly rotating the drive shaft when the drive motor assembly is activated.

In another embodiment, a mixing element is disposed within the compartment of the flexible bag and coupled with the drive shaft.

In another embodiment, the mixing element comprises an impeller.

In another embodiment, the invention further comprises:
  a rotational assembly comprising an outer casing secured to the flexible bag and a tubular hub rotatably disposed within the outer casing, a passage extending through the tubular hub;
  an impeller disposed within the compartment of the flexible bag;
  a tubular member extending between the hub of the rotational assembly and the impeller; and
  a drive shaft engaged with the drive motor assembly and the impeller and passing through the tubular hub and tubular member.

In a second independent aspect of the present invention, a liquid mixing system includes:
  a support housing at least partially bounding a compartment;
  a mount secured to the support housing;
  a drive motor assembly configured to engage a drive shaft for moving the drive shaft within the compartment of the support housing; and
  a four bar linkage system extending between the mount and the drive motor assembly, the four bar linkage system being movable between a first position wherein the drive motor assembly is disposed at a first elevation and a second position wherein the drive motor assembly is disposed at a second elevation that is different from the first elevation.

In one embodiment, the four bar linkage system automatically changes the angular orientation of the drive motor assembly as the drive motor assembly is moved from the first elevation to the second elevation.

In another embodiment, the angular orientation of the drive motor assembly changes by at least 1° and more commonly at least 2° 3°, 4°, 5°, or 6° as the drive motor assembly is moved from the first elevation to the second elevation.

In another embodiment, the four bar linkage system comprises four arms each having a first end hingedly connected to the drive motor assembly and an opposing second end hingedly connected to the mount.

In another embodiment, the invention further comprises:
  a support extending between two of the four arms of the four bar linkage system; and
  a drive assembly extending between the mount and the support.

In another embodiment, the drive assembly comprises a hydraulic or pneumatic piston.

In another embodiment, the mount comprises:
  an elongated first rail spanning across the top opening and having opposing ends secured to the support housing;
  an elongated second rail spanning across the top opening and having opposing ends secured to the support housing, the second rail being spaced apart from the first rail;
  a brace extending between the first rail and the second rail so as to be disposed over the top opening.

In another embodiment, the first rail and the second rail are U-shaped or arch shaped and upwardly project from the support housing.

In another embodiment, a drive assembly extends between the brace and the four bar linkage system and controls movement of the four bar linkage system.

In another embodiment, the drive assembly comprises a hydraulic or pneumatic piston.

In another embodiment, the support housing has an annular flange that encircles the top opening, the mount being secured on opposing sides of the annular flange so that the mount spans entirely across the top opening.

In another embodiment, a container is disposed within the chamber of the support housing, the container bounding a compartment and being coupled to the drive motor assembly.

In another embodiment, a drive shaft is coupled with the drive motor assembly, at least a portion of the drive shaft being disposed within the compartment of the container, the drive motor assembly rotating the drive shaft when the drive motor assembly is activated.

In another embodiment, a mixing element is disposed within the compartment of the container and coupled with the drive shaft.

In another embodiment, the mixing element comprises an impeller.

In another embodiment, the invention further comprises:
  a rotational assembly comprising an outer casing secured to the container and a tubular hub rotatably disposed within the outer casing, a passage extending through the tubular hub;
  an impeller disposed within the compartment of the flexible bag;
  a tubular member extending between the hub of the rotational assembly and the impeller; and
  a drive shaft engaged with the drive motor assembly and the impeller and passing through the tubular hub and tubular member.

The second aspect of the invention may also include any of the features, options and possibilities set out elsewhere in this document, including in or associated with the above first or below third aspect of the invention.

In a third independent aspect of the present invention, a method for mixing a liquid includes:
  moving a mixing element disposed at a first location within a compartment of a container so as to mix a first volume of a liquid within the compartment;
  adding liquid to the compartment of the container so as to form a second volume of the liquid within the compartment;
  moving a four bar linkage system so as to raise the mixing element within the compartment of the container to a second position; and
  moving the mixing element at the second position so as to mix the second volume of liquid within the container.

In one embodiment, moving the mixing element comprises rotating the mixing element.

In another embodiment, the mixing element comprises an impeller.

In another embodiment, the step of moving the four bar linkage system automatically adjusts an angular orientation of the mixing element.

In another embodiment, the angular orientation of the mixing element is moved by an angle of at least 1°, 2°, 3°, 4°, 5°, 7°, 10°, 15°, or 20° as the mixing element is moved from the first position to the second position.

In another embodiment, the mixing element is moved by a vertical distance of at least or less than 5 cm, 10 cm, 20 cm, 40 cm, or 60 cm as it is moved from the first position to the second position.

In another embodiment, the invention further comprises:
a support housing at least partially bounding a compartment;
a mount secured to the support housing;
a drive motor assembly;
a drive shaft coupled with the drive motor assembly, the mixing element being coupled to the drive shaft; and
the four bar linkage system comprising four arms each having a first end hingedly connected to the drive motor assembly and an opposing second end hingedly connected to the mount.

In another embodiment, the step of moving a four bar linkage system comprises pivoting each of the four arms.

In another embodiment, the step of moving a four bar linkage system comprises moving a piston extending between the mount and the four bar linkage system.

The third aspect of the invention may also include any of the features, options and possibilities set out elsewhere in this document, including in or associated with the above first and second aspect of the invention.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

DETAILED DESCRIPTION OF THE PREFERRED EMBODIMENTS

Figure 1:
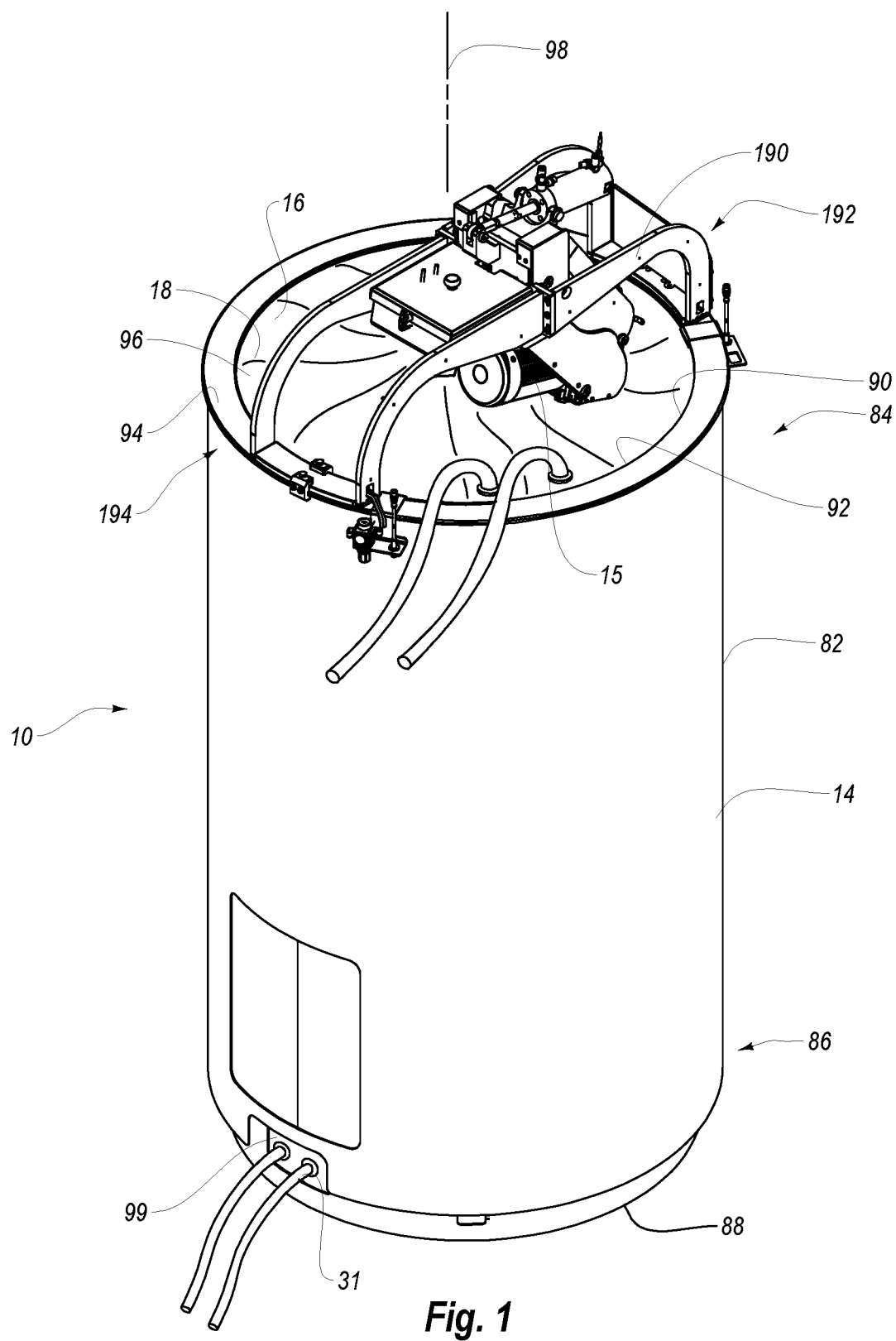
FIG. 1 is a perspective view of a fluid mixing system.

Before describing the present disclosure in detail, it is to be understood that this disclosure is not limited to parameters of the particularly exemplified systems, methods, apparatus, products, processes, compositions, and/or kits, which may, of course, vary. It is also to be understood that the terminology used herein is only for the purpose of describing particular embodiments of the present disclosure, and is not necessarily intended to limit the scope of the disclosure in any particular manner. Thus, while the present disclosure will be described in detail with reference to specific embodiments, features, aspects, configurations, etc., the descriptions are illustrative and are not to be construed as limiting the scope of the claimed invention. Various modifications can be made to the illustrated embodiments, features, aspects, configurations, etc. without departing from the spirit and scope of the invention as defined by the claims. Thus, while various aspects and embodiments have been disclosed herein, other aspects and embodiments are contemplated.

Unless defined otherwise, all technical and scientific terms used herein have the same meaning as commonly understood by one of ordinary skill in the art to which the present disclosure pertains. While a number of methods and materials similar or equivalent to those described herein can be used in the practice of the present disclosure, only certain exemplary materials and methods are described herein.

Various aspects of the present disclosure, including devices, systems, methods, etc., may be illustrated with reference to one or more exemplary embodiments or implementations. As used herein, the terms "embodiment," "alternative embodiment" and/or "exemplary implementation" means "serving as an example, instance, or illustration," and should not necessarily be construed as preferred or advantageous over other embodiments or implementations disclosed herein. In addition, reference to an "implementation" of the present disclosure or invention includes a specific reference to one or more embodiments thereof, and vice versa, and is intended to provide illustrative examples without limiting the scope of the invention, which is indicated by the appended claims rather than by the following description.

It will be noted that, as used in this specification and the appended claims, the singular forms "a," "an" and "the" include plural referents unless the content clearly dictates otherwise. Thus, for example, reference to a "rail" includes one, two, or more rails. Similarly, reference to a plurality of referents should be interpreted as comprising a single referent and/or a plurality of referents unless the content and/or context clearly dictate otherwise. Thus, reference to "rails" does not necessarily require a plurality of such rails. Instead, it will be appreciated that independent of conjugation; one or more rails are contemplated herein.

As used throughout this application the words "can" and "may" are used in a permissive sense (i.e., meaning having the potential to), rather than the mandatory sense (i.e., meaning must). Additionally, the terms "including," "having," "involving," "containing," "characterized by," variants thereof (e.g., "includes," "has," and "involves," "contains," etc.), and similar terms as used herein, including the claims, shall be inclusive and/or open-ended, shall have the same meaning as the word "comprising" and variants thereof (e.g., "comprise" and "comprises"), and do not exclude additional, un-recited elements or method steps, illustratively.

Various aspects of the present disclosure can be illustrated by describing components that are coupled, attached, connected, and/or joined together. As used herein, the terms "coupled", "attached", "connected," and/or "joined" are used to indicate either a direct connection between two components or, where appropriate, an indirect connection to one another through intervening or intermediate components. In contrast, when a component is referred to as being "directly coupled", "directly attached", "directly connected," and/or "directly joined" to another component, no intervening elements are present or contemplated. Thus, as used herein, the terms "connection," "connected," and the like do not necessarily imply direct contact between the two or more elements. In addition, components that are coupled, attached, connected, and/or joined together are not necessarily (reversibly or permanently) secured to one another. For instance, coupling, attaching, connecting, and/or joining can comprise placing, positioning, and/or disposing the components together or otherwise adjacent in some implementations.

As used herein, directional and/or arbitrary terms, such as "top," "bottom," "front," "back," "left," "right," "up," "down," "upper," "lower," "inner," "outer," "internal," "external," "interior," "exterior," "proximal," "distal" and the like can be used solely to indicate relative directions and/or orientations and may not otherwise be intended to limit the scope of the disclosure, including the specification, invention, and/or claims.

Where possible, like numbering of elements have been used in various figures. In addition, similar elements and/or elements having similar functions may be designated by similar numbering (e.g., element "10" and element "210.") Furthermore, alternative configurations of a particular element may each include separate letters appended to the element number. Accordingly, an appended letter can be used to designate an alternative design, structure, function, implementation, and/or embodiment of an element or feature without an appended letter. Similarly, multiple instances of an element and or sub-elements of a parent element may each include separate letters appended to the element number. In each case, the element label may be used without an appended letter to generally refer to instances of the element or any one of the alternative elements. Element labels including an appended letter can be used to refer to a specific instance of the element or to distinguish or draw attention to multiple uses of the element. However, element labels including an appended letter are not meant to be limited to the specific and/or particular embodiment(s) in which they are illustrated. In other words, reference to a specific feature in relation to one embodiment should not be construed as being limited to applications only within said embodiment.

It will also be appreciated that where a range of values (e.g., less than, greater than, at least, and/or up to a certain value, and/or between two recited values) is disclosed or recited, any specific value or range of values falling within the disclosed range of values is likewise disclosed and contemplated herein. Thus, disclosure of an illustrative measurement or distance less than or equal to about 10 units or between 0 and 10 units includes, illustratively, a specific disclosure of: (i) a measurement of 9 units, 5 units, 1 units, or any other value between 0 and 10 units, including 0 units and/or 10 units; and/or (ii) a measurement between 9 units and 1 units, between 8 units and 2 units, between 6 units and 4 units, and/or any other range of values between 0 and 10 units.

It is also noted that systems, methods, apparatus, devices, products, processes, compositions, and/or kits, etc., according to certain embodiments of the present invention may include, incorporate, or otherwise comprise properties, features, aspects, steps, components, members, and/or elements described in other embodiments disclosed and/or described herein. Thus, reference to a specific feature, aspect, steps, component, member, element, etc. in relation to one embodiment should not be construed as being limited to applications only within said embodiment. In addition, reference to a specific benefit, advantage, problem, solution, method of use, etc. in relation to one embodiment should not be construed as being limited to applications only within said embodiment.

The headings used herein are for organizational purposes only and are not meant to be used to limit the scope of the description or the claims. To facilitate understanding, like reference numerals have been used, where possible, to designate like elements common to the figures.

The present invention relates to systems and methods for mixing liquid fluids such as solutions or suspensions. The systems can be commonly used as bioreactors or fermentors for culturing cells or microorganisms. By way of example and not by limitation, the inventive systems can be used in culturing bacteria, fungi, algae, plant cells, animal cells, protozoan, nematodes, and the like. The systems can accommodate cells and microorganisms that are aerobic or anaerobic and are adherent or non-adherent. The systems can also be used in association with the formation and/or treatment of solutions and/or suspensions that are for biological purposes, such as media, buffers, or reagents. For example, the systems can be used in the formation of media where sparging is used to control the pH of the media through adjustment of the carbonate/bicarbonate levels with controlled gaseous levels of carbon dioxide. The systems can also be used for mixing powders or other components into a liquid where sparging is not required and/or where the solution/suspension is not for biological purposes.

Depicted in FIG. 1 is one embodiment of an inventive mixing system 10 incorporating features of the present invention. In general, mixing system 10 comprises a support housing 14, a container assembly 16 that is supported within support housing 14, a drive motor assembly 15 mounted on support housing 14 and a drive shaft 17 (FIG. 3) that extends between drive motor assembly 15 and container assembly 16. Container assembly 16 houses the liquid that is mixed and otherwise processed. The various components of mixing system 10 will now be discussed in greater detail.

Figure 2:
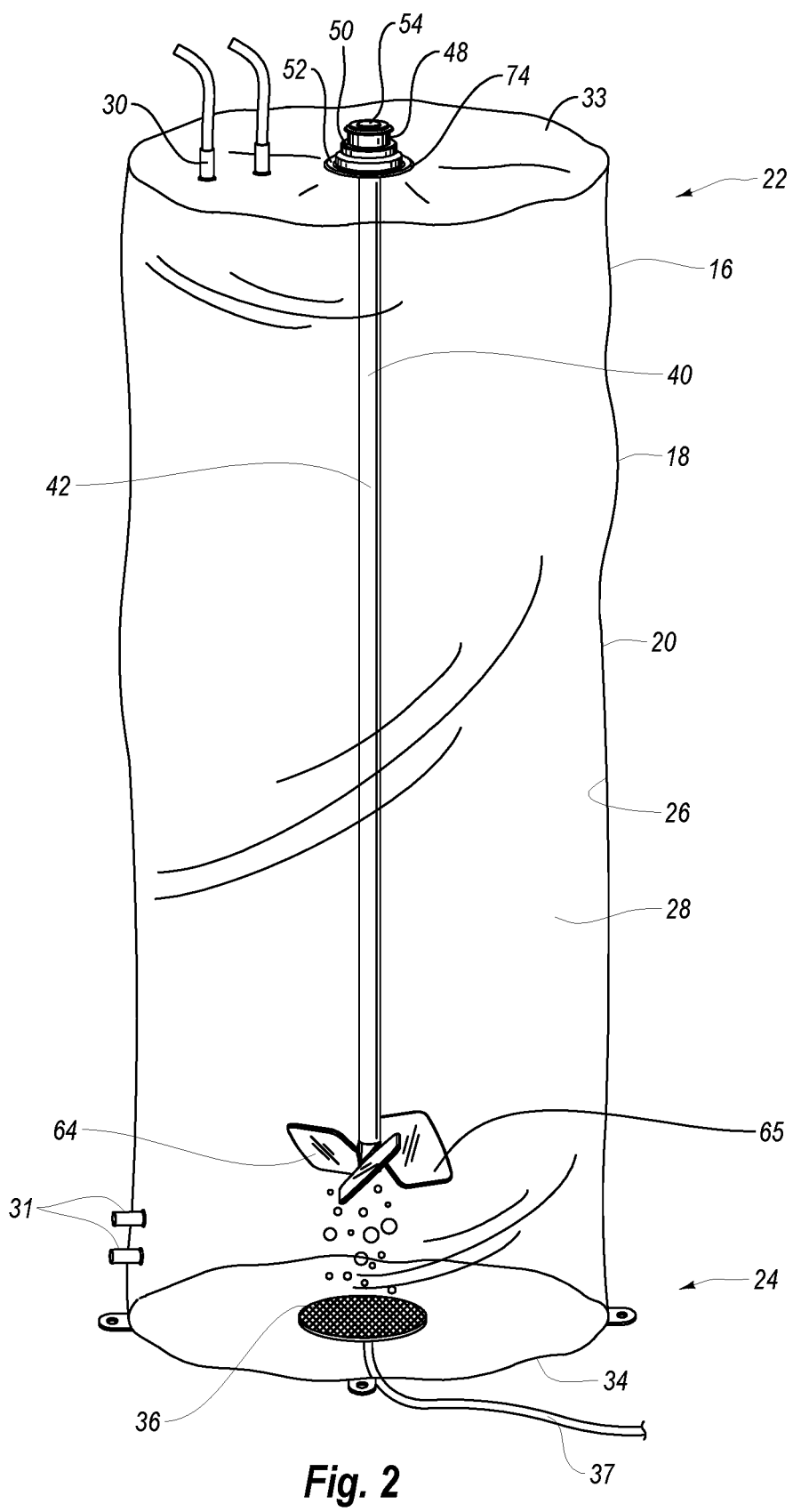
FIG. 2 is a perspective view of the container assembly of the fluid mixing system shown in FIG. 1.

As depicted in FIG. 2, container assembly 16 comprises a container 18 having a side 20 that extends from an upper end 22 to an opposing lower end 24. Upper end 22 terminates at an upper end wall 33 while lower end 24 terminates at a lower end wall 34. Container 18 also has an interior surface 26 that bounds a compartment 28. Compartment 28 is configured to hold a fluid. In the embodiment depicted, container 18 comprises a flexible, collapsible bag that is comprised of one or more sheets of a flexible, water impermeable polymeric film such as a low-density polyethylene. The polymeric film can have a thickness that is at least or less than 0.02 mm, 0.05 mm, 0.1 mm, 0.2 mm, 0.5 mm, 1 mm, 2 mm, 3 mm or in a range between any two of the foregoing. Other thicknesses can also be used. The film is sufficiently flexible that it can be rolled into tube without plastic deformation and can be folded over an angle of at least 90°, 180°, 270°, or 360° without plastic deformation.

The film can be comprised of a single ply material or can comprise two or more layers which are either sealed together or separated to form a double wall container. Where the layers are sealed together, the material can comprise a laminated or extruded material. The laminated material comprises two or more separately formed layers that are subsequently secured together by an adhesive. One example of an extruded material that can be used in the present invention is the Thermo Scientific CX3-9 film available from Thermo Fisher Scientific. The Thermo Scientific CX3-9 film is a three-layer, 9 mil cast film produced in a cGMP facility. The outer layer is a polyester elastomer coextruded with an ultra-low density polyethylene product contact layer. Another example of an extruded material that can be used in the present invention is the Thermo Scientific CX5-14 cast film also available from Thermo Fisher Scientific. The Thermo Scientific CX5-14 cast film comprises a polyester elastomer outer layer, an ultra-low density polyethylene contact layer, and an EVOH barrier layer disposed therebetween.

The material can be approved for direct contact with living cells and be capable of maintaining a solution sterile. In such an embodiment, the material can also be sterilizable such as by ionizing radiation. Examples of materials that can be used in different situations are disclosed in U.S. Pat. No. 6,083,587 which issued on Jul. 4, 2000 and United States Patent Publication No. US 2003-0077466 A1, published Apr. 24, 2003, which are hereby incorporated by specific reference.

In one embodiment, container 18 can comprise a two-dimensional pillow style bag. In another embodiment, container 18 can be formed from a continuous tubular extrusion of polymeric material that is cut to length. The ends can be seamed closed or panels can be sealed over the open ends to form a three-dimensional bag. Three-dimensional bags not only have an annular side wall but also a two dimensional top end wall and a two dimensional bottom end wall. Three dimensional containers can comprise a plurality of discrete panels, typically three or more, and more commonly four to six. Each panel is substantially identical and comprises a portion of the side wall, top end wall, and bottom end wall of the container. Corresponding perimeter edges of each panel are seamed together. The seams are typically formed using methods known in the art such as heat energies, RF energies, sonics, or other sealing energies.

In alternative embodiments, the panels can be formed in a variety of different patterns. Further disclosure with regard to one method of manufacturing three-dimensional bags is disclosed in United States Patent Publication No. US 2002-0131654 A1, published Sep. 19, 2002, which is incorporated herein by specific reference in its entirety.

It is appreciated that container 18 can be manufactured to have virtually any desired size, shape, and configuration. For example, compartment 28 of container 18 can have a volume of at least or less than 10 liters, 30 liters, 100 liters, 250 liters, 500 liters, 750 liters, 1,000 liters, 1,500 liters, 3,000 liters, 5,000 liters, 10,000 liters or in a range between any two of the foregoing. Other volumes can also be used. Although container 18 can be any shape, in one embodiment container 18 is specifically configured to be generally complementary to the chamber on support housing 14 in which container 18 is received so that container 18 is properly supported within the chamber.

Although in the above discussed embodiment container 18 is depicted as a flexible bag, in alternative embodiments it is appreciated that container 18 can comprise any form of collapsible container or disposable container. Container 18 can also be transparent or opaque.

Continuing with FIG. 2, formed on container 18 are a plurality of ports 30 at upper end 22 and a plurality of ports 31 at lower end 24. Each of ports 30, 31 communicate with compartment 28. Although only a few ports 30, 31 are shown, it is appreciated that container 18 can be formed with any desired number of ports 30, 31 and that ports 30, 31 can be formed at any desired location on container 18. Ports 30, 31 can be the same configuration or different configurations and can be used for a variety of different purposes. For example, ports 30, 31 can be coupled with fluid lines for delivering media, cell cultures, and/or other components into container 18 and withdrawing fluid from container 18. Ports 30, 31 can also be used for delivering gas to container 18, such as through a sparger, and withdrawing gas from container 18.

Ports 30, 31 can also be used for coupling probes and/or sensors to container 18. For example, when container 18 is used as a bioreactor or fermentor for growing cells or microorganisms, ports 30, 31 can be used for coupling probes such as temperature probes, pH probes, dissolved oxygen probes, and the like. Various optical sensors and other types of sensors can also be attached to ports 30, 31. Examples of ports 30, 31 and how various probes, sensors, and lines can be coupled thereto is disclosed in United States Patent Publication No. 2006-0270036, published Nov. 30, 2006 and United States Patent Publication No. 2006-0240546, published Oct. 26, 2006, which are incorporated herein by specific reference in their entirety. Ports 30, 31 can also be used for coupling container 18 to secondary containers, to condenser systems, and to other desired fittings.

Mounted on lower end wall 34 is a sparger 36 having a gas line 37 coupled thereto. Sparger 36 is designed to deliver gas bubbles to the culture or other liquid within container 18 for oxygenating and/or regulating content of various gases within the culture/fluid. As needed, a second or more spargers can be mounted on lower end wall 34. The spargers can be the same or different configurations. For example, one sparger can be designed to deliver small bubbles for oxygenating while a second sparger can be designed to deliver larger bubbles for stripping $CO_2$ from the culture/fluid. In some forms of the invention, one of the spargers can be an open tube or a tube with a porous frit with relatively large pores, while the other sparger can be a tube with a porous frit with relatively small pores. The sparger can also comprise a perforated or porous membrane that is mounted on the end of a port or on the interior surface of lower end wall 34 so as to extend over a port. It is appreciated that spargers come in a variety of different configurations and that any type of spargers can be used as desired or as appropriate for the expected culture volumes, cells, fluids and other conditions. In some uses of mixing system 10, a sparger may not be required and thus sparger 36 can be eliminated.

It is appreciated that the various gas lines, fluid lines, spraging lines, drain lines and/or the like can be coupled to container 18 at the time of manufacture so that they can be sterilized concurrently with container 18. Alternatively, the lines can be connected to container 18 either prior to or after inserting container 18 into support housing 14. The lines can be connected to container 18 using commonly known aseptic connectors.

Figure 3:
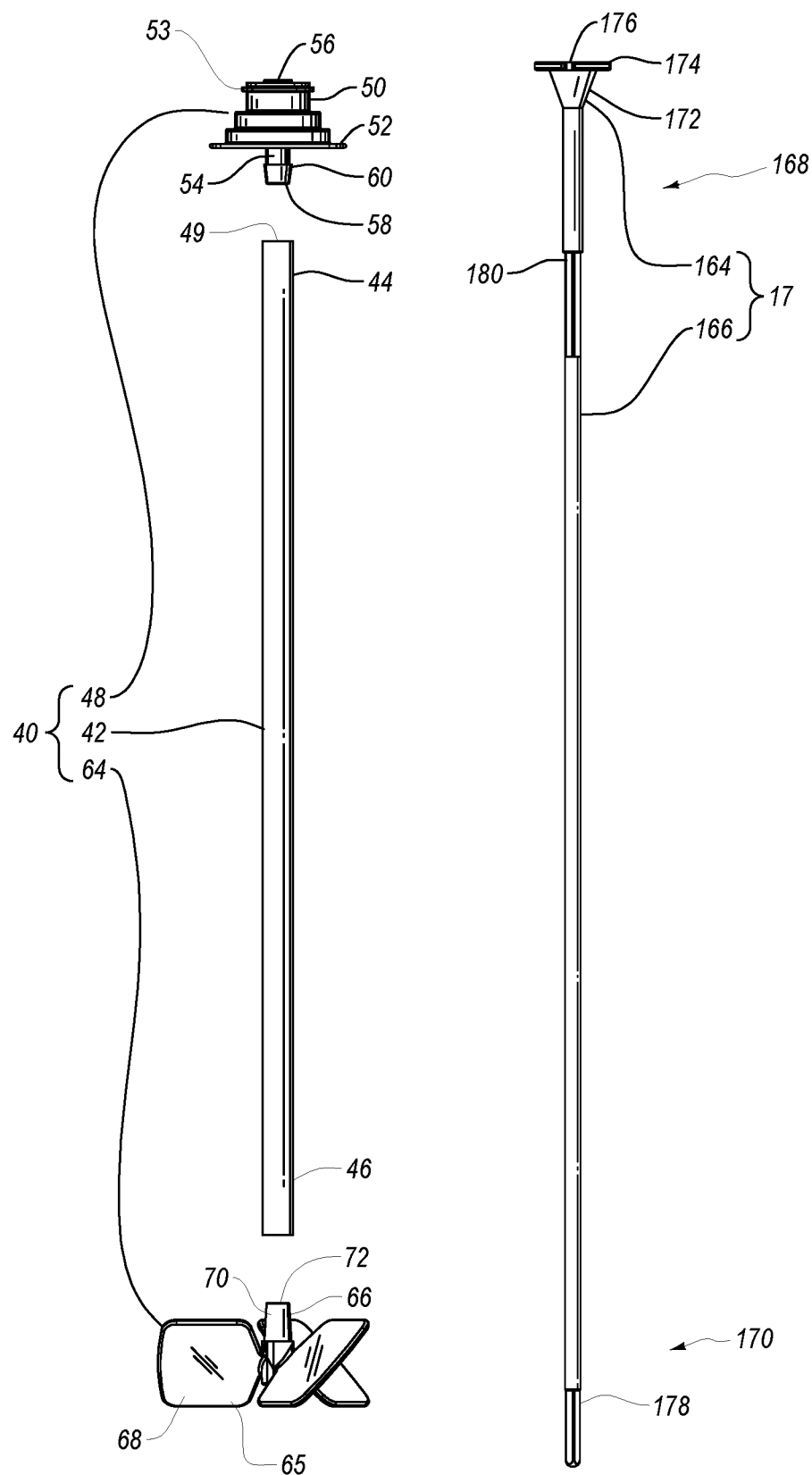
FIG. 3 is an exploded view of the mixing assembly shown in FIG. 2 and the drive shaft used therewith.

Container assembly 16 further comprises a mixing assembly 40. As depicted in FIG. 3, mixing assembly 40 comprises an elongated tubular connector 42 having a rotational assembly 48 mounted at one end and a mixing element 64 mounted on the opposing end. More specifically, tubular connector 42 has a first end 44 and an opposing second end 46 with a passage 49 that extends therebetween. In one embodiment, tubular connector 42 comprises a flexible tube such as a polymeric tube. In one embodiment, the tube is sufficiently flexible that it can be bent along its longitudinal axis over an angle of at least 90°, 180°, 270°, or 360° without plastic deformation.

Tubular connector 42 is typically made from, comprises or consists of a sufficiently flexible material, such as an elastomeric material, so that tubular connector can withstand repeated bending and deformation without appreciable structural yield and can possess a durometer on the Shore OO scale that is typically less than 98 and often less than 60 or 30. Other values can also be used. Tubular connector 42 can be formed from a polymeric material such flexible PVC or other polymers having the desired properties. In other embodiments, tubular connector 42 can comprise a rigid tube or a combination of rigid and flexible tubes.

Figure 4:
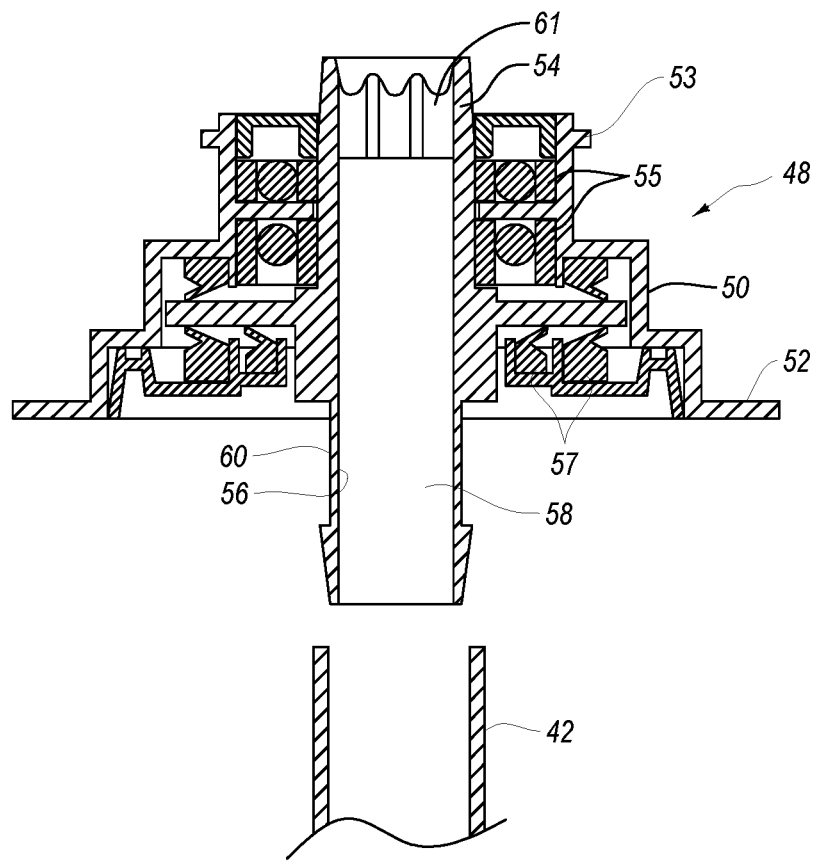
FIG. 4 is a cross sectional side view of the rotational assembly of the mixing assembly shown in FIG. 3.

Rotational assembly 48 is mounted to first end 44 of tubular connector 42. As depicted in FIG. 4, rotational assembly 48 comprises an outer casing 50 having an outwardly projecting annular sealing flange 52 and an outwardly projecting mounting flange 53. A tubular hub 54 is rotatably disposed within outer casing 50. One or more bearing assemblies 55 can be disposed between outer casing 50 and hub 54 to permit free and easy rotation of hub 54 relative to casing 50. Likewise, one or more seals 57 can be formed between outer casing 50 and hub 54 so that during use an aseptic seal can be maintained between outer casing 50 and hub 54.

Hub 54 has an interior surface 56 that bounds an opening 58 extending therethrough. As will be discussed below in greater detail, interior surface 56 includes an engaging portion 61 having a polygonal or other non-circular transverse cross section so that a driver portion 180 of drive shaft 17 (FIG. 3) passing through opening 58 can engage engaging portion 61 and facilitate rotation of hub 54 by rotation of drive shaft 17. Hub 54 can also comprise a tubular stem 60 projecting away from outer casing 50. Returning to FIG. 3, hub 54 can couple with first end 44 of tubular connector 42 by stem 60 being received within first end 44. A pull tie, clamp, crimp or other fastener can then be used to further secure stem 60 to tubular connector 42 so that a liquid tight seal is formed therebetween. Other conventional connecting techniques can also be used.

In one embodiment, mixing element 64 comprises an impeller 65 having a central hub 66 with a plurality of blades 68 radially outwardly projecting therefrom. In the embodiment depicted, blades 68 are integrally formed as a unitary structure with hub 66. In other embodiments, blades 68 can be separately attached to hub 66. It is appreciated that a variety of different numbers and configurations of blades 68 can be mounted on hub 66. Hub 66 has a first end 70 with a blind socket 72 formed thereat. Socket 72 typically has a noncircular transverse cross section, such as polygonal, so that it can engage a driver portion 178 of drive shaft 17. Accordingly, as will be discussed below in greater detail, when driver portion 178 is received within socket 72, driver portion 178 engages with impeller 65 such that rotation of drive shaft 17 facilities rotation of impeller 65.

Impeller 65 can be attached to connector 42 by inserting first end 70 of hub 66 within connector 42 at second end 46. A pull tie, clamp, crimp, or other type of fastener can then be cinched around second end 46 of connector 42 so as to form a liquid tight sealed engagement between impeller 65 and connector 42. In other embodiment, mixing element 64 can comprise a stir bar, paddle, or other mixing element that when rotated, reciprocated, or otherwise moved by drive shaft 17 will mix the liquid within container 18.

Turning to FIG. 2, rotational assembly 48 is secured to container 18 so that tubular connector 42 and mixing element 64 extend into or are disposed within compartment 28 of container 18. Specifically, in the depicted embodiment container 18 has an opening 74 at upper end 22. Sealing flange 52 of outer casing 50 is sealed around the perimeter edge bounding opening 74 so that hub 54 is aligned with opening 74. Tubular connector 42 having mixing element 64 mounted on the end thereof projects from hub 54 into compartment 28 of container 18. In this configuration, outer casing 50 is fixed to container 18. Thus, hub 54, tubular connector 42 and impeller 65 can freely rotate relative to outer casing 50 and container 18. As a result of rotational assembly 48 sealing opening 74, compartment 28 is sealed closed so that it can be used in processing sterile fluids.

As depicted in FIG. 3, mixing assembly 40 is used in conjunction with drive shaft 17. In general drive shaft 17 comprises a head section 164 and a shaft section 166 that can be integrally formed as a single continuous member or can comprise a plurality of sections that are coupled together such as by threaded connection or other techniques. Drive shaft 17 can be comprised of high strength polymers, ceramics, composites, metals, such as aluminum, stainless steel, or other metal alloys, or other materials. Shaft section 166 has a first end 168 and an opposing second end 170. Disposed at first end 168 is head section 164 which comprises a frustoconical engaging portion 172 that terminates at an outwardly extending circular plate 174. Notches 176 are formed on a perimeter edge of circular plate 174 and are used for engaging drive shaft 17 with drive motor assembly 15 as will be discussed below.

Formed at second end 170 of drive shaft 17 is driver portion 178. Driver portion 178 has a non-circular transverse cross section so that it can facilitate locking engagement within hub 66 of impeller 65 as discussed above. In the embodiment depicted, driver portion 178 has a polygonal transverse cross section. However, other non-circular shapes can also be used. Driver portion 180 is also formed on shaft section 166 at or toward first end 168. Driver portion 180 also has a non-circular transverse cross section and is positioned so that it can facilitate locking engagement within engaging portion 61 (FIG. 4) of rotational assembly 48 as discussed above.

During use, as will be discussed below in further detail, drive shaft 17 is advanced down through hub 54 of rotational assembly 48, through tubular connecter 42 and into hub 66 of impeller 65. As a result of the interlocking engagement of driver portions 178 and 180 with hubs 66 and 54, respectively, rotation of drive shaft 17 by drive motor assembly 15 (FIG. 1) facilitates rotation of hub 54, tubular connecter 42 and impeller 65 relative to outer casing 50 of rotational assembly 48 and container 18. As a result of the rotation of impeller 65 or other mixing element 64, liquid within container 18 is mixed.

In an alternative embodiment, drive shaft 17 can be formed from 2, 3, 4, 5 or more sections that are selectively coupled together. Furthermore, different sections can be made of different materials. By forming drive shaft 17 from multiple sections, it is easy to form a shaft having a desired length by adding or removing sections. Furthermore, the modular drive shaft 17 can be used in a room with a low ceiling height. For example, a first section of drive shaft 17 can be partially advanced down through drive motor assembly 15. Additional sections can then be progressively attached thereto as the sections are progressively advanced down through drive motor assembly 15. Accordingly, the full length of drive shaft 17 need not be simultaneously raised above drive motor assembly 15 for passing therethrough. Alternative embodiments of drive shafts that can be used in the present inventive system, including examples of how separate sections can be coupled together, are disclosed in U.S. Pat. No. 8,641,314 which issued on Feb. 4, 2014 and which is incorporated herein by specific reference.

It is appreciated that mixing assembly 40, drive shaft 17 and the discrete components thereof can have a variety of different configurations and can be made of a variety of different materials. Alternative embodiments of and further disclosure with respect to mixing assembly 40, drive shaft 17, and the components thereof are disclosed in U.S. Pat. No. 7,384,783, issued Jun. 10, 2008 and US Patent Publication No. 2011/0188928, published Aug. 4, 2011 which are incorporated herein in their entirety by specific reference.

Returning to FIG. 1, support housing 14 has a substantially cylindrical sidewall 82 that extends between an upper end 84 and an opposing lower end 86. Lower end 86 has a floor 88 mounted thereto. As a result, support housing 14 has an interior surface 90 that bounds a chamber 92. An annular flange 94 is formed at upper end 84 and bounds an access opening 96 to chamber 92. As discussed above, chamber 92 is configured to receive container assembly 16 so that container 18 is supported therein.

Although support housing 14 is shown as having a substantially cylindrical configuration, in alternative embodiments support housing 14 can have any desired shape capable of at least partially bounding a compartment. For example, sidewall 82 need not be cylindrical but can have a variety of other transverse, cross sectional configurations such as polygonal, elliptical, or irregular. Furthermore, it is appreciated that support housing 14 can be scaled to any desired size. For example, it is envisioned that support housing 14 can be sized so that chamber 92 can hold a volume of less than 50 liters, more than 10,000 liters or any of the other volumes or range of volumes as discussed above with regard to container 18. Support housing 14 is typically made of metal, such as stainless steel, but can also be made of other materials capable of withstanding the applied loads of the present invention.

While support housing 14 can have any desired dimensions, in one embodiment support housing 14 can be elongated with a relatively small diameter. Specifically, when mixing system 10 is used as a fermentor, it is desirable to have a high mixing rate of the culture within container 18 to maintain consistent oxygenation and nutrient content throughout the culture. The mixing efficiency is increased by support housing 14 and corresponding container 18 having a relatively small diameter so that the culture is maintained relatively close to impeller 65. Because the diameter is relatively small, to enable batch processing at traditional volumes, the height of support housing 14 and corresponding container 18 can be long relative to the diameter. Having a relatively tall support housing 14 and corresponding container 18 also increases the resident time of the sparged gas bubbles within container 18, thereby increasing the mass transfer of the gas into the fluid. Again, this has increased importance where mixing system 10 is used as a fermentor.

By way of example and not by limitation, chamber 92 of support housing 14 can have a central longitudinal axis 98 that extends through floor 88 and access opening 96. Chamber 92 can have a maximum transverse diameter D that is normal to axis 98 and a height H that that extends along longitudinal axis 98 between floor 88 and access opening 96. Chamber 92 can be made with diameter D being between about 15 cm to about 225 cm and a corresponding height H being between about 35 cm to about 500 cm. The ratio of height H to diameter D to can be in a range between about 1 to about 10 with about 1.2 to about 4 and about 1.6 to about 3.3 being more common. In some embodiments, the ratio can be at least, or less than 1.5, 2, 2.5, 3, 4, 5 or in a range between any two of the foregoing. Again, other dimensions and ratios can also be used depending on the intended use for mixing system 10. It is appreciated that the diameters and heights as discussed above with regard to support housing 14 are also applicable to the diameter and height of container 18 when positioned within support housing 14. In addition, by making support housings 14 elongated with a relatively small diameter, mixing system 10 can be passed through normal or narrow doorways through which traditionally sized mixing system would not fit. As such, mixing systems 10 can be used in a broader range of locations.

Extending through sidewall 82 of support housing 14 at lower end 86 is an opening 99. Opening 99 is designed to receive ports 31 and the tube or fittings attached thereto. As previously mentioned, any number of ports 31 can be formed on container 18. In turn, as also previously discussed, sensors, probes, fluid lines, and the like can be coupled with ports 31 so as to communicate with compartment 28 of container 18.

In one embodiment of the present invention means are provided for regulating the temperature of the liquid that is contained within container 18 when container 18 is disposed within support housing 14. By way of example and not by limitation, sidewall 82 can be jacketed so as to bound one or more fluid channels that encircle sidewall 82 and that communicate with an inlet port and an outlet port. A fluid, such as water or propylene glycol, can be pumped into the fluid channel through the inlet port. The fluid then flows in a pattern around sidewall 82 and then exits out through the outlet port.

By heating or otherwise controlling the temperature of the fluid that is passed into the fluid channel, the temperature of support housing 14 can be regulated which in turn regulates the temperature of the fluid within container 18 when container 18 is disposed within support housing 14. In an alternative embodiment, electrical heating elements can be mounted on or within support housing 14. The heat from the heating elements is transferred either directly or indirectly to container 18. Alternatively, other conventional means can also be used such as by applying gas burners to support housing 14 or pumping the fluid out of container 18, heating the fluid and then pumping the fluid back into container 18. When using container 18 as part of a bioreactor or fermentor, the means for heating can be used to heat the culture within container 18 to a temperature in a range between about 30° C. to about 40° C. Other temperatures can also be used.

Figure 5:
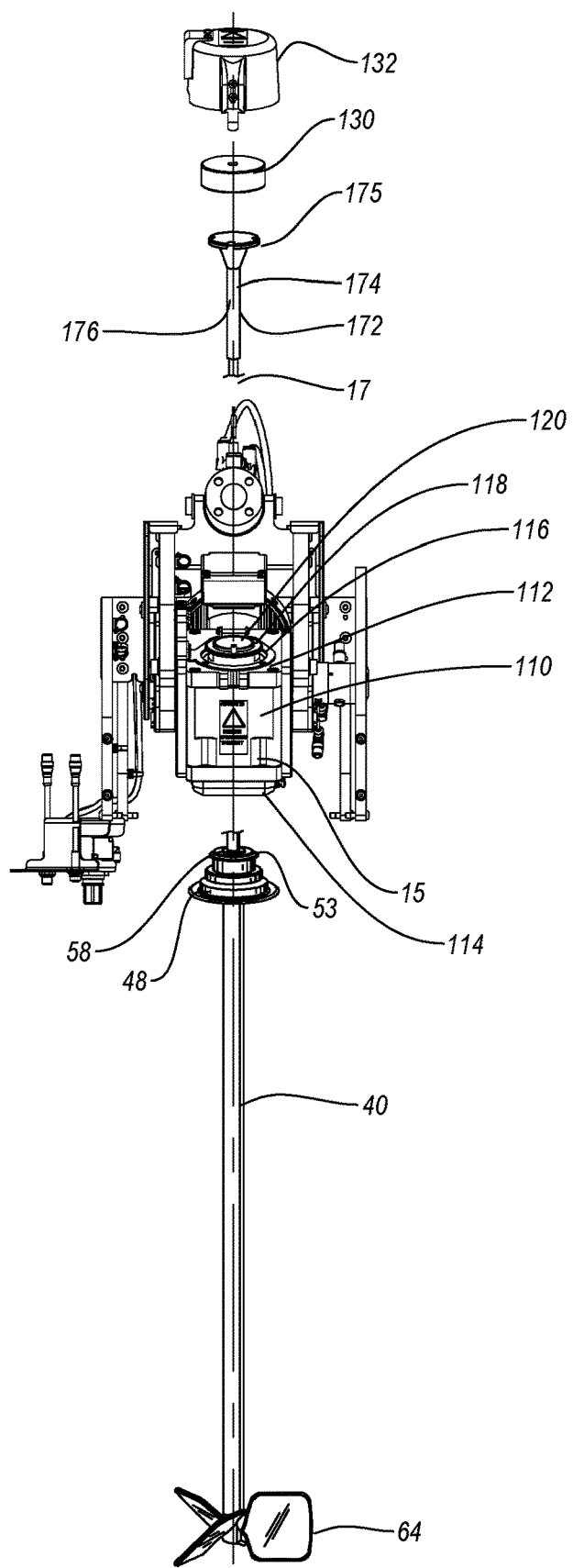
FIG. 5 is a partially exploded front view of the mixing assembly and drive shaft shown in FIG. 3 aligned for use with the drive motor assembly.
Figure 6:
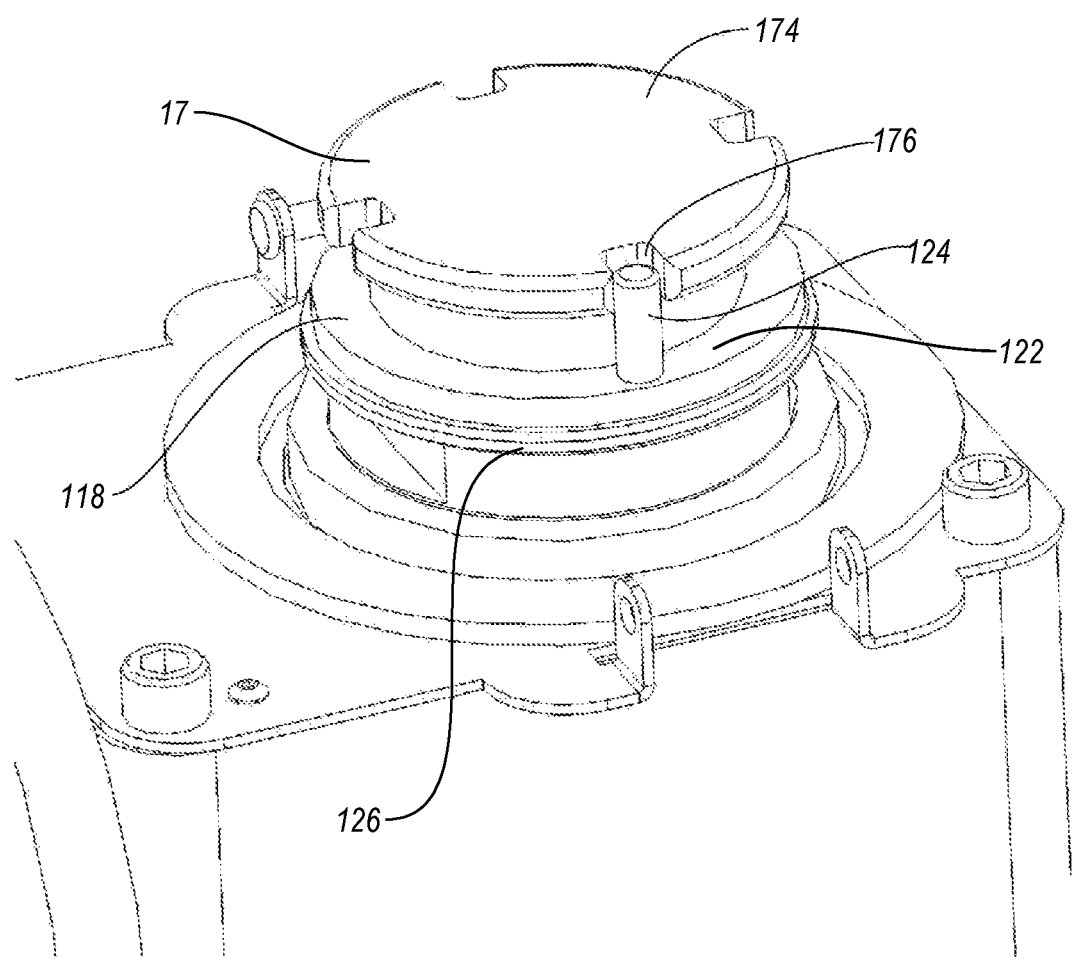
FIG. 6 is an enlarged top perspective view of the drive motor assembly shown in FIG. 5 with the drive shaft coupled thereto.
Figure 10:
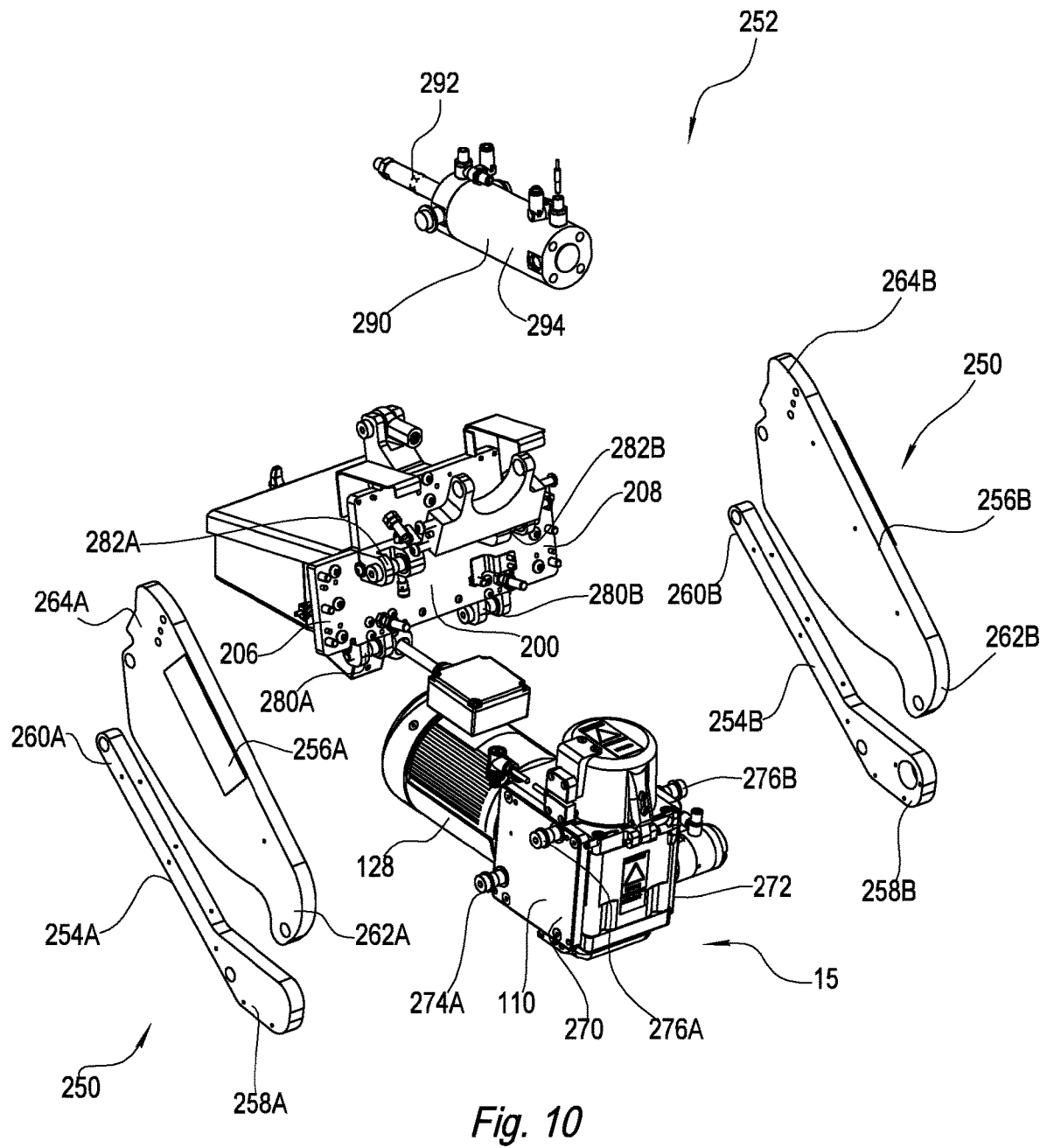
FIG. 10 is an exploded view of the four bar linkage system shown in FIG. 8 and the drive motor assembly.

Turning to FIG. 5, drive motor assembly 15 comprises a housing 110 having a top surface 112 and an opposing bottom surface 114 with an opening 116 extending through housing 110 between surfaces 112 and 114. A tubular motor mount 118 is rotatably secured within opening 116 of housing 110 and bounds a passage 120 extending therethrough. As depicted in FIG. 6, the upper end of motor mount 118 terminates at an end face 122 having a locking pin 124 outwardly projecting therefrom. A thread 126 encircles motor mount 118 adjacent to end face 122. A drive motor 128, as depicted in FIG. 10, is mounted to housing 110 and engages with motor mount 118 so as to facilitate select rotation of motor mount 118 relative to housing 110. Drive motor 128 typically comprises an electrical motor. A belt, gear, linkage, drive shaft or any other mechanism can be used to transfer energy from drive motor 128 to motor mount 118 to facilitate select rotation of motor mount 118. The rotation can be continuous in one direction or reciprocating.

Drive shaft 17 is configured to pass through motor mount 118 and thus through housing 110. The upper end of passage 120 extending through motor mount 118 forms an engaging portion having a frustoconical configuration that is complementary to frustoconical engaging portion 172 (FIG. 3) of drive shaft 17. As a result, the two engaging portions can be complementarily mated to facilitate contacting engagement between motor mount 118 and drive shaft 17 when drive shaft 17 is passed through motor mount 118 as depicted in FIG. 6.

When drive shaft 17 is passed through motor mount 118, plate 174 rests on or slightly above end face 122 of motor mount 118 so that locking pin 124 is received within a notch 176 thereof. As a result, drive shaft 17 is locked to motor mount 118 so that rotation of motor mount 118 facilitates concurrent rotation of drive shaft 17. A cap 130 (FIG. 5) can be threaded onto the end of motor mount 118 to prevent drive shaft 17 from disengaging from motor mount 118. In turn, a protective cover 132 can be placed over cap 130 and secured to housing 110.

Figure 7:
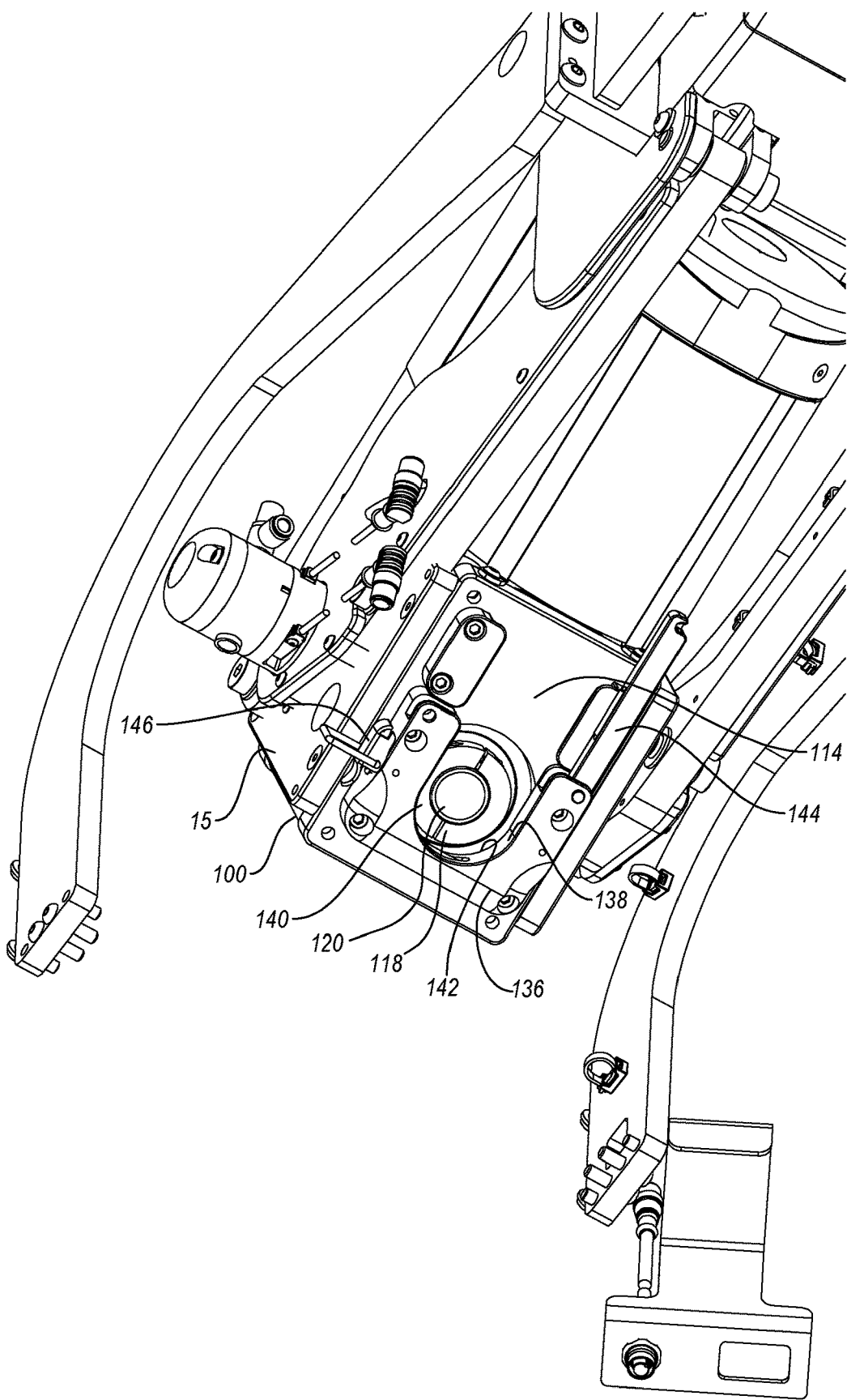
FIG. 7 bottom perspective view of the drive motor assembly shown in FIG. 5.

Turning to FIG. 7, disposed on bottom surface 114 of housing 110 of drive motor assembly 15 is a restrainer 136. Restrainer 136 has a U-shaped interior surface 138 that bounds a U-shaped receiving slot 140 that passes through restrainer 136. Receiving slot 140 is aligned with passage 120 extending through motor mount 118 so that drive shaft 17 can pass therethrough. A U-shaped catch slot 142 is recessed on interior surface 138 and extends along the length thereof. Receiving slot 140 is configured so that rotational assembly 48 (FIG. 3) can be laterally slid into receiving slot 140 so that opening 58 passing through hub 54 is aligned with passage 120 extending through motor mount 118. As rotational assembly 48 is laterally slid into receiving slot 140, mounting flange 53 of rotational assembly 48 is received within catch slot 142 so that rotational assembly 48 is retained within receiving slot 140.

A gate 144 is hingedly mounted to restrainer 136 and can be selectively moved between an open position and a closed position. In the open position, as shown in FIG. 7, gate 144 is rotated away from receiving slot 140 so that rotational assembly 48 can be freely laterally slid into or out of receiving slot 140. Once rotational assembly 48 is disposed within receiving slot 140, gate 144 can be rotated to the closed position where gate 144 spans across the lateral opening of receiving slot 140 and thereby locks rotational assembly 48 within receiving slot 140. A latch 146 and can engage and secure gate 144 in the closed position.

Accordingly, to facilitate attachment of rotational assembly 48 to housing 100, gate 144 is rotated to the open position and rotational assembly 48 is horizontally or laterally slid into receiving slot 140 of restrainer 136 so that mounting flange 53 of rotational assembly 48 is received within catch slot 142. Rotational assembly 48 is advanced into receiving slot 140 so that opening 58 of rotational assembly 48 (FIG. 3) aligns with passage 120 extending through motor mount 118. In this position, gate 144 is moved to the closed position and secured in place by latch 146 so that rotational assembly 48 is locked to drive motor assembly 15. Further discussion of drive motor assembly 15 and how it engages with drive shaft 17 and alternative designs of drive motor assembly 15 are discussed in US Patent Publication No. 2011/0188928 which was previously incorporated herein by specific reference.

As depicted in FIG. 1, drive motor assembly 15 is secured to support housing 14 by a mount 190. Mount 190 has a first end 192 secured to flange 94 at a first location and an opposing second end 194 that is secured to flange 94 at a second location. The first and second locations are on opposing sides of access opening 96 so that mount 190 spans across access opening 96. In other embodiments, flange 94 can be eliminated and the opposing ends of mount 190 can be secured directly to upper end 84 of support housing 14 or upper end 84 of sidewall 82. Furthermore, flange 94 need not completely encircle access opening 96 but could comprise a U- or C-shaped section or two, three, or more spaced apart sections that are mounted on sidewall 82.

Figure 8:
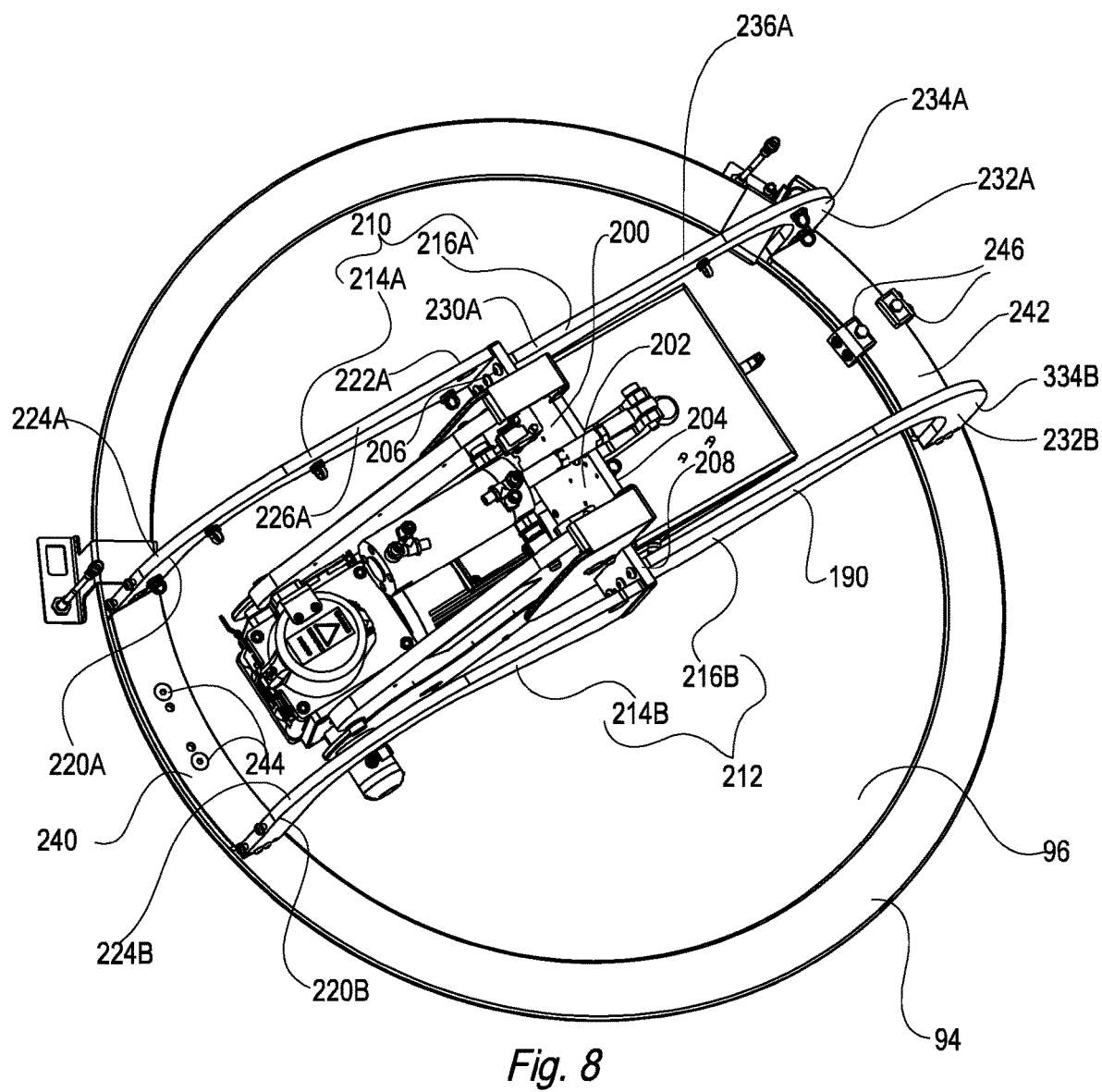
FIG. 8 is a top perspective view of the drive motor assembly, mount, and four bar linkage system shown in FIG. 1, attached to the annular flange of the support housing.
Figure 9:
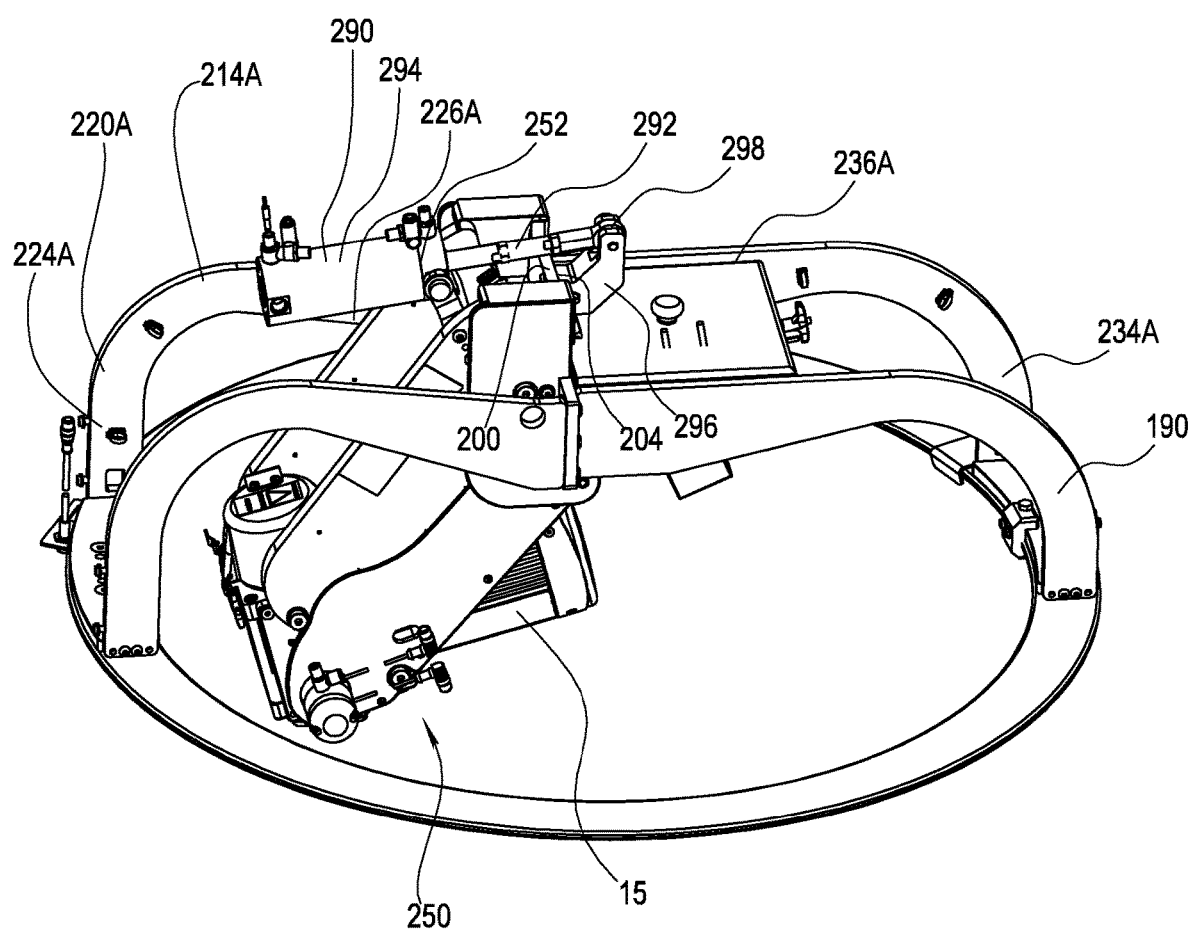
FIG. 9 is a side perspective view of the components in FIG. 8.

As depicted in FIGS. 8 and 9, mount 190 comprises a brace 200 having a first side 202 and an opposing second side 204 which each extend between a first end 206 and an opposing second end 208. In one embodiment, brace 200 comprises a plate but other structures can also be used. Mount 190 also comprises a first rail 210 and a spaced apart second rail 212 that both span across access opening 96 and connect to flange 94 on opposing sides thereof. Brace 200 is centrally connected to first rail 210 and second rail 212 and spans therebetween so that brace 200 is centrally supported over access opening 96. Brace 200 can be disposed so as to be vertically oriented, i.e., sides 202 and 204 are disposed in planes that are vertically orientated, or disposed at an angle that is less than +/−30°, 20°, or 10° relative to vertical. In this configuration, mount 190 has an H-shaped configuration.

In one embodiment, first rail 210 and second rail 212 can each comprise a single, unitary continuous rail. In the depicted embodiment, however, first rail 210 comprises a first forward rail 214A and a first rear rail 216A while second rail 212 comprises a second forward rail 214B and a second rear rail 216B. First forward rail 214A has a first end 220A connected to flange 94 at a first location and an opposing second end 222A that is connected to brace 200 and particularly to first side 202 of brace 200. First forward rail 214A has a generally L-shaped configuration that includes a foot 224A located at first end 220A and a leg 226A extending from foot 224A and connecting to brace 200. Foot 224A has a longitudinal axis that typically upwardly projects at an angle of at least 45°, 60°, 75°, or 90° relative to the horizontal while leg 226A has a longitudinal axis that typically projects horizontally or at an angle less than 30°, 20°, or 10° relative to the horizontal.

Similarly, first rear rail 216A has a first end 230A that is connected to brace 200 and particularly to second side 204 of brace 200 and an opposing second end 232A connected to flange 94 at a second location. First rear rail 216A has a generally L-shaped configuration that includes a foot 234A located at second end 232A and a leg 236A extending from foot 234A and connecting to brace 200. Foot 234A has a longitudinal axis that typically upwardly projects at an angle of at least 45°, 60°, 75°, or 90° relative to the horizontal while leg 236A has a longitudinal axis that typically projects horizontally or at an angle less than 30°, 20°, 10° relative to the horizontal. Based on the above, first rail 210 can be described as being a substantially U or arched shaped member that extends between first end 220A and an opposing second end 232A having feet 224A and 234A disposed at the opposing ends and a single leg extending therebetween. Again, the feet and leg can extend as discussed above. Where first rail 210 is integrally formed a single, continuous member, brace 200 can attach thereto such as by welding, or through the use of fasteners, either directly or through the use of a bracket. Other techniques can also be used.

Second forward rail 214B and second rear rail 216B have the same configurations and alternatives as first forward rail 214A and first rear rail 216A, respectively, as discussed above. As such, like reference elements between rails 214A and 214B and between rails 216A and 216B are identified by like reference characters except that all of the elements of rails 214B and 216B are identified by a letter "B" rather than the letter "A". Accordingly, second rail 212 can also be described as being a substantially U or arched shaped member that extends between first end 220B and an opposing second end 232B having feet 224B and 234B disposed at the opposing ends and a single leg extending therebetween. Again, the feet and leg can extend as discussed above. Where second rail 212 is integrally formed a single, continuous member, brace 200 can attach thereto such as by welding, or through the use of fasteners, either directly or through the use of a bracket. Other techniques can also be used. In this configuration, mount 190, rails 210, 212 and or brace 200 can project vertically above flange 94 or support housing 14 by as distance of at least 10 cm, 20 cm, 30 cm, 40, cm, 50 cm or more. This vertical spacing enables all or at least part of dive motor assembly 15 to be retained outside of compartment 28 of container 18.

Extending between first end 220A of first rail 210 and first end 220B of second rail 212 is a first mounting brace 240 while extending between second end 232A of first rail 210 and second end 232B of second rail 212 is a second mounting brace 242. Mounting braces 240 and 242 are used to removably secure mount 190 to support housing 14. For example, fasteners 244, such as screws, bolts, pins, or the like are shown removably coupling first mounting brace 240 to flange 94. In contrast, clamps 246 are shown removably coupling second mounting brace 242 to flange 94. In one embodiment of the present invention, means are provided for removably securing mount 190 to support housing 14. Fasteners 244 and clamps 246 are examples of such means. Other examples of means that can be used include catches, latches, ties, couplings, and other types of joiners. In other embodiments, it is appreciated that mounting braces 240 and 242 can be eliminated and the opposing ends of one or both of rails 210 and 212 can be directly secured to flange 94 using one or more of the above techniques.

As a result of mount 190 being removably attached to support housing 14, mixing system 10 become more modular. For example, support housing 14 can be used with or without mount 190 and connected drive motor assembly 15. Furthermore, mount 190 and connected drive motor assembly 15 can be easily attached or retrofitted onto preexisting support housings 14. In addition, if drive motor assembly 15 needs to be repaired or replaced with a different size, the combined mount 190 and drive motor assembly 15 can be easily removed and repaired or replaced. Other benefits also exist. However, in other embodiments, it is also appreciated that mount 190 could be permanently attached to flange 94, such as by welding.

In on embodiment of the present invention, drive motor assembly 15 is secured to mount 190 so that drive motor assembly 15 can be selectively raised and lowered between at least a first position and a second position. In addition, drive motor assembly 15 can be secured to mount 190 so that drive motor assembly 15 is disposed at a first angular orientation when in the first position and is disposed at a second angular orientation when in the second position, the second angular orientation being different from the first angular orientation. By way of example and not by limitation, as depicted in FIG. 9, a four bar linkage system 250 used in association with a drive assembly 252 can be used to movably secure drive motor assembly 15 to mount 190.

As depicted in FIG. 10, linkage system 250 comprises a first lower arm 254A and a first upper arm 256A that are disposed on a first side of drive motor assembly 15 and a second lower arm 254B and second upper arm 256B that are disposed on an opposing second side of drive motor assembly 15. First lower arm 254A is elongated and extends between a first end 258A and an opposing second end 260A. First upper arm 256A is also elongated and extends between a first end 262A and an opposing second end 264A. Second lower arm 254B and second upper arm 256B are substantially the same configuration as first lower arm 254A and first upper arm 256A, respectively, and thus like element between arms 254A and 254B and between arms 256A and 256B are identified by like reference characters except that the elements for arms 254B and 256B are identified with the letter "B".

Housing 110 of drive motor assembly 15 has a first side face 270 disposed on a first side of housing 110 and an opposing second side face 272 disposed on an opposing second side of housing 110. A first lower pivot pin 274A and a first upper pivot pin 276A project from first side face 270 with pin 276A being disposed vertically above pin 274A. A corresponding, second lower pivot pin 274B and second upper pivot pin 276B (FIG. 11) also project from second side face 272 with pin 276B being disposed vertically above pin 274B. In addition, as depicted in FIG. 10, a first lower pivot pin 280A and a first upper pivot pin 282A are disposed on first end of 206 of brace 200, with pin 282A disposed above pin 280A, and a second lower pivot pin 280B and a second upper pivot pin 282B are disposed on second end of 208 of brace 200, with pin 282B disposed above pin 280B.

Figure 11:
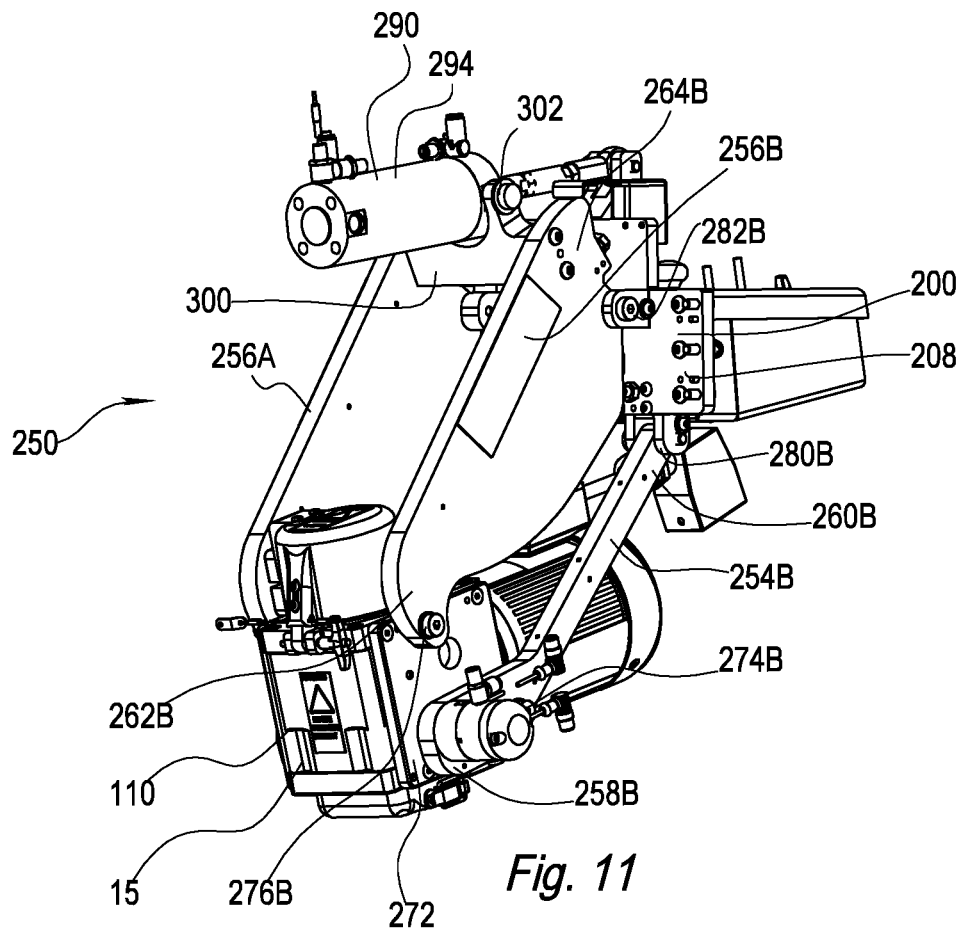
FIG. 11 is a right side perspective view of the four bar linkage system coupled to the drive motor assembly.
Figure 12:
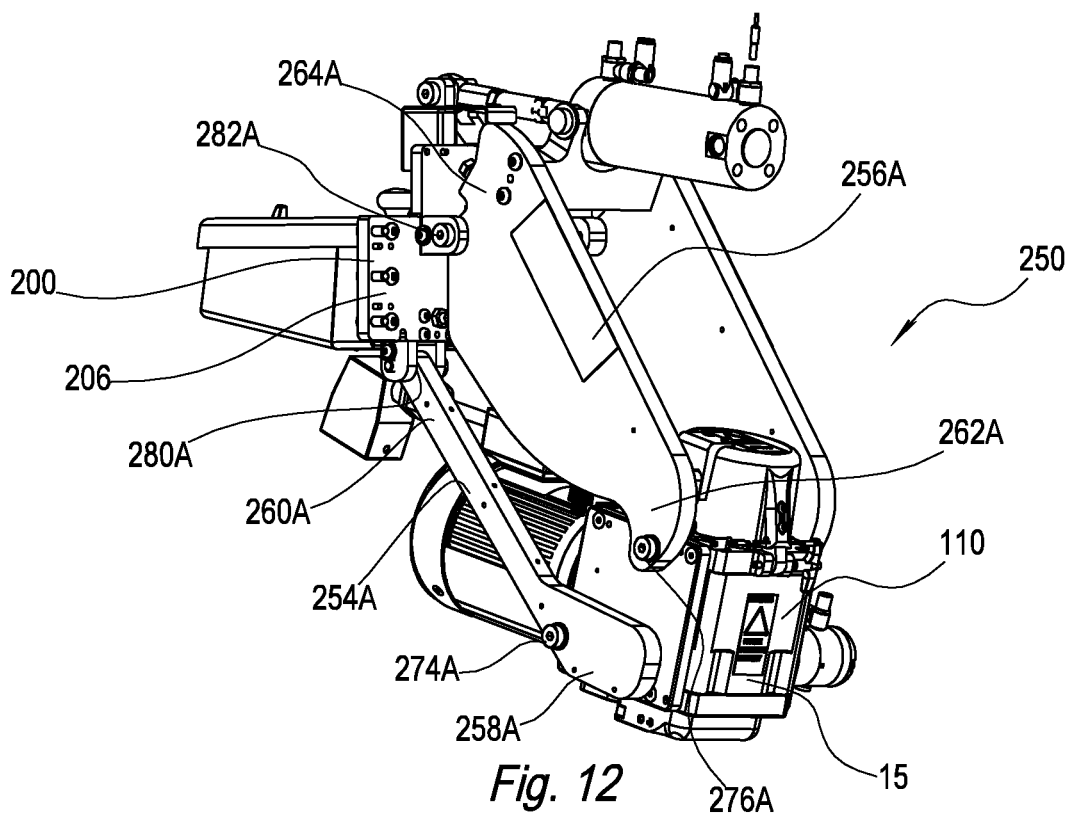
FIG. 12 is a left side perspective view of the four bar linkage system coupled to the drive motor assembly.

In the assembled state as depicted in FIGS. 11 and 12, first end 258A of first lower arm 254A is hingedly attached to the first side of housing 110 and, more particularly, first end 258A is rotatably attached to first side face 270 (FIG. 10) by being rotatably secured to first lower pivot pin 274A or by being secured to first lower pivot pin 274A which is rotatable relative to housing 110. Likewise, second end 260A of first lower arm 254A is hingedly attached to first end 206 of brace 200 and, more particularly, second end 260A is rotatably attached to brace 200 by being rotatably secured to first lower pivot pin 280A or by being secured to first lower pivot pin 280A which is rotatable relative to brace 200.

First end 258B of second lower arm 254B is hingedly attached to the second side of housing 110 and, more particularly, first end 258B is rotatably attached to second side face 272 by being rotatably secured to second lower pivot pin 274B or by being secured to second lower pivot pin 274B which is rotatable relative to housing 110. Likewise, second end 260B of second lower arm 254B is hingedly attached to second end 208 of brace 200 and, more particularly, second end 260B is rotatably attached to brace 200 by being rotatably secured to second lower pivot pin 280B or by being secured to second lower pivot pin 280B which is rotatable relative to brace 200.

First end 262A of first upper arm 256A is hingedly attached to the first side of housing 110 and, more particularly, first end 262A is rotatably attached to first side face 270 by being rotatably secured to first upper pivot pin 276A or by being secured to first upper pivot pin 276A which is rotatable relative to housing 110. Likewise, second end 264A of first upper arm 256A is hingedly attached to first end 206 of brace 200 and, more particularly, second end 264A is rotatably attached to brace 200 by being rotatably secured to first upper pivot pin 282A or by being secured to first upper pivot pin 282A which is rotatable relative to brace 200.

Finally, first end 262B of second upper arm 256B is hingedly attached to the second side of housing 110 and, more particularly, first end 262B is rotatably attached to second side face 272 by being rotatably secured to second upper pivot pin 276B or by being secured to second upper pivot pin 276B which is rotatable relative to housing 110. Likewise, second end 264B of second upper arm 256B is hingedly attached to second end 208 of brace 200 and, more particularly, second end 264B is rotatably attached to brace 200 by being rotatably secured to second upper pivot pin 282B or by being secured to second upper pivot pin 282B which is rotatable relative to brace 200.

In the above assembled configuration, drive motor assembly 15 can be selectively raised and lowered between at least two positions. For example, in FIG. 13 arms 254 and 256 are all pivoted to a lowered position and thus drive motor assembly 15 is in a lowered position. However, in FIG. 14 arms 254 and 256 are upwardly pivoted to a raised position and thus drive motor assembly 15 is in a raised position which is at an elevation higher than the lowered position. Thus, by pivoting arms 254 and 256 of four bar linkage system 250, drive motor assembly 15 can be selectively raised and lowered between the raised position and the lowered position and to any location therebetween.

Drive assembly 252 is used to control movement of four bar linkage system 250. In one embodiment, as depicted in FIG. 10, drive assembly 252 comprises a piston 290. Piston 290 includes a piston rod 292 that moves within a cylinder 294. Piston 290 can comprise a pneumatic or hydraulic piston. As depicted in FIG. 9, piston rod 292 is hingedly coupled to mount 190 or brace 200 thereof. More specifically, a stay 296 is mounted to second side 204 of brace 200. An exposed first end of piston rod 292 is hingedly attached to stay 296 by a hinge 298. In turn, cylinder 294 is connected to linkage system 250. More specifically, as depicted in FIG. 11, a support 300 is secured to and extends between first and second upper arms 256A and 256B. Cylinder 294 is hingedly connected to support 300 by a hinge 302.

Figure 13:
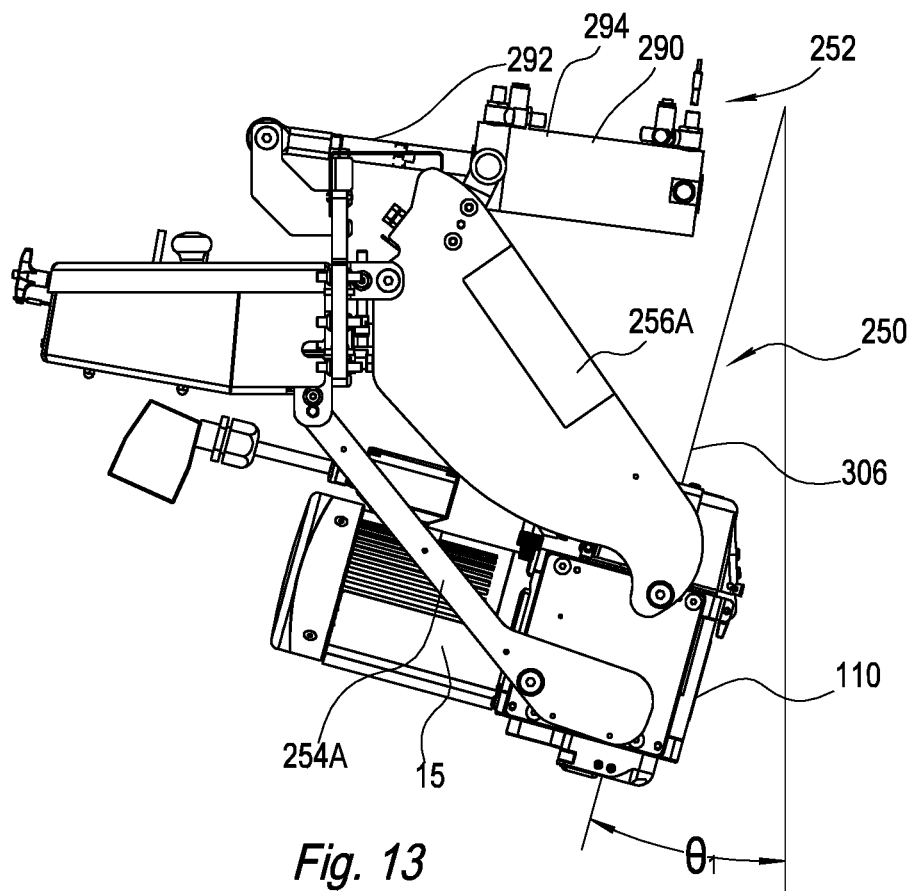
FIG. 13 is a left side view of the four bar linkage system holding the drive motor assembly in a lowered position.
Figure 14:
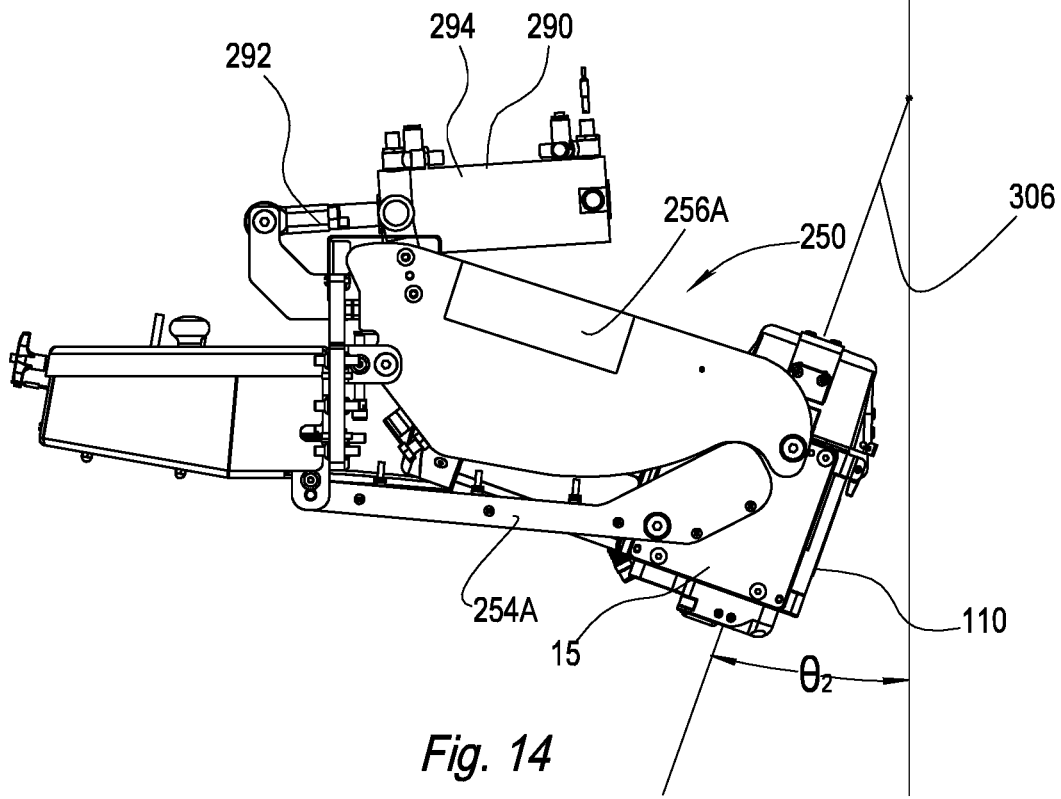
FIG. 14 is a left side view of the four bar linkage system holding the drive motor assembly in a raised position.

Accordingly, drive assembly 252 can be selectively activated to lower linkage system 250 and thus move drive motor assembly 15 into the lowered position, as depicted in FIG. 13, or raise linkage system 250 and thus move drive motor assembly 15 into the raised position, as depicted in FIG. 14. More specifically, when drive assembly 252 is activated to advance rod 292 out of cylinder 294, the arms of linkage system 250 are rotated downward and thus move drive motor assembly 15 into the lowered position. In turn, when drive assembly 252 is activated to retract rod 292 into cylinder 294, the arms of linkage system 250 are rotated upward and thus move drive motor assembly 15 into the raised position.

In an alternative embodiment, the orientation of piston 290 can be reversed so that cylinder 294 is connected to mount 190 and rod 292 is connected to linkage system 250. It is appreciated that a variety of other mechanical configurations can be used to raise and lower linkage system 250. For example, in other embodiments drive assembly 252 could comprise a gear assembly, pulley system, belt assembly or other movement system that is operated electrically, pneumatically, or hydraulically. Thus, drive assembly 252 can be selectively movable between an expanded and retracted position and have a first end coupled, such as hingedly, to mount 190 and have an opposing second end coupled, such as hingedly, to linkage system 250.

The vertical height by which drive motor assembly 15 (and also drive shaft 17 and mixing element 64 attached thereto) moves as it transfers between the lowered and raised position can vary based on factors such as the length of the arms of linkage system 250. However, in one embodiment, drive motor assembly 15, drive shaft 17, and or mixing element 64 can move vertically by a distance of at least or less than 5 cm, 10 cm, 20 cm, 40 cm, 60 cm or in a range between any two of the foregoing as drive motor assembly 15 is moved between the lowered and raised positions.

Furthermore, one of the benefits of using linkage system 250 to raise and lower drive motor assembly 15 is that linkage system 250 can be configured to retain drive motor assembly 15 in the same angular orientation as it is moved between the lowered and raised positions or it can be configured to change the angular orientation of drive motor assembly 15 as it is moved between the lowered and raised positions. For example, as depicted in FIG. 13, a central longitudinal axis 306 of passage 120 of motor mount 118 (FIG. 7) is shown passing through housing 110. Central longitudinal axis 306 is aligned with or extends parallel to the central longitudinal axis of drive shaft 17 (FIG. 3) when drive shaft 17 is passed down through passage 120. When drive motor assembly 15 is in the lowered position shown in FIG. 13, and angle $\theta_1$ is formed between axis 306 and the vertical. When drive motor assembly 15 is in the raised position shown in FIG. 14, an angle $\theta_2$ is formed between axis 306 and the vertical. By modifying the configuration of linkage system 250, such as by modifying the length and orientation of arms 254 and 256, angle $\theta_2$ can be the same as, larger than, or smaller than angle $\theta_1$. For example, the difference between angle $\theta_1$ and angle $\theta_2$ can be at least or less than 1°, 2°, 3°, 4°, 5°, 7°, 10°, 15°, 20° or in a range between any two of the foregoing. The angle $\theta_1$ and $\theta_2$ can each be at least or less than 1°, 3°, 5°, 7°, 10°, 15°, 20°, 25°, 30°, 35°, 40° or in a range between any two of the foregoing. The above angles and changes in the angle or orientation are also application to drive shaft 17 and mixing element 64 which are connected to drive motor assembly 15.

It can be desirable to change the angle orientation of drive motor assembly 15, drive shaft 17, and/or mixing element 64 to ensure that mixing element 64 is retained in a desired position within container 18 for optimal or desired mixing of the liquid therein as drive motor assembly 15, drive shaft 17, and/or mixing element 64 are raised and lowered. For example, when drive motor assembly 15 is in the lowered position, shown in FIG. 13, mixing element 64 attached to drive shaft 17 may be centrally positioned within container 18 for optimal mixing of the liquid therein. As drive motor assembly 15 is moved from the lowered position to the raised position, shown in FIG. 14, the operation of linkage system 250 causes drive motor assembly 15 to move forward, i.e., toward sidewall 82 of support housing 14, as drive motor assembly 15 is being raised. As a result, drive shaft 17 and mixing element 64 are also moved forward. However, by concurrently changing the angular orientation of drive motor assembly 15, and thus also the angular orientation of drive shaft 17 and mixing element 64, mixing element 64 can be retained centrally within container 18 or otherwise moved to a desired lateral position for optimal or desired mixing of the fluid at that desired elevation.

One advantage of being able to selectively adjust the vertical height and tilt or angular orientation of mixing element 64 and drive shaft 17 through the use of linkage system 250 is that mixing system 10 can be used to maintain optimal mixing conditions of fluid within a single container assembly 16 over a relatively large change in fluid volumes. Specifically, the preferred position for mixing element 64 within container 18 to achieve optimal mixing can be determined using conventional techniques. This position can be measured as a height from the bottom of container assembly 16 and is subject to the height of the fluid within container assembly 16. Thus, as the fluid level increases within container assembly 16, the height of the location for mixing element 64 to achieve optimal mixing also increases and vice-a-versa. Maintaining mixing element 64 at the optimal location for mixing helps to ensure that the fluid is homogeneous. This can be especially helpful where mixing system 10 is functioning as a bioreactor or fermentor. In that case, the media, additives, and cells or microorganisms should be continually turned over and homogeneously dispersed to ensure that all of the cells and microorganisms are being continuously and uniformly fed and oxygenated.

It is also common that the volume of fluid within container assembly 16 will vary significantly. For example, when first starting a bioreactor or fermentor, the seed inoculum of cells or microorganisms can be dispersed into a rather small volume of media within container assembly 16. As the cells/microorganisms grow and multiply, more media and additives can be progressively added to container assembly 16. By using the inventive system, the seed inoculum can be delivered into a relatively large container assembly 16 although only a small volume of media is initially being used. In this initial step, mixing element 64 is lowered to achieve optimal mixing of the initial volume. As more fluid is progressively added into container 18, mixing element 64 is progressively raised to maintain optimal mixing for the defined fluid volume. When the culturing is complete or it is otherwise desired to remove the solution or suspension from container assembly 16, mixing element 64 can again be progressively lowered as the fluid within container assembly 16 is progressively lowered. During the mixing process, it is typically preferred to maintain a positive gas pressure within container assembly 16, such as in a range from 0.05 psi to about 2 psi to keep container assembly 16 away from the moving mixing element 64 and to keep container 18 against heated support housing 14 to maintain temperature regulation. This can be more important during low volume processing.

The ability to progressively add and remove relatively large amounts of liquid from a single container while maintaining optimal mixing of the liquid eliminates or at least decreases the need to transfer the solution to different sized containers for processing. By using a single container for processing as opposed to moving the fluid between different sized containers, the inventive system decreases processing down time, avoids the expense of unnecessary containers, minimizes the risk of contamination, and minimizes potential damage to cells/microorganisms. The inventive system can operate over a relatively high turn-down ratio. A "turn-down ratio" is the ratio of maximum to minimum volumes of fluid that a single container can process while maintaining acceptable mixing conditions. For example, a turn-down ratio of 10:1 means that if the initial volume that a mixing system can process at acceptable mixing conditions is 10 liters, the volume of fluid with the container can be increased by a factor of 10, i.e., up to 100 liters, and the system would still be able to process the fluid at acceptable mixing conditions. By using inventive mixing system 10 as a bioreactor, fermentor, or other system that requires mixing or suspension it is appreciated that container assembly 16 can be sized to operate with a turn-down ratio of at least 2:1, 3:1, 4:1, 5:1, 6:1, 8:1, 10:1, 15:1, 20:1 or in a range between any two of the foregoing.

What constitutes acceptable mixing conditions is in part dependent upon what is being processed. When the system is functioning as a bioreactor or fermentor growing cells or microorganisms, the mixing should, in general, assist in dispersal of the cells/microorganisms and sparged gas throughout the solution so that the cells/microorganisms have access to the required nutrients in the media and proper mass transfer is achieved with the sparged gas. However, the mixing should not be so severe as to apply unwanted shear forces to the cells/microorganisms, create undesired splashing, or cause cavitation or a vortex in the solution, all of which can hamper the growth of cells/microorganisms.

Another advantage of one embodiment of the present invention is that four bar linkage system 250 automatically and concurrently adjusts the tilt or angular orientation of drive motor assembly 15, drive shaft 17 and/or mixing element 64 so that mixing element 64 is at the optimal or desired position for mixing liquid within container 18 as drive motor assembly 15, drive shaft 17 and/or mixing element 64 are moved between the lowered and raised position. As such, no separate calculation or adjustment is required by the operator to ensure that mixing element 64 is properly laterally positioned as mixing element is vertically adjusted.

A method of assembly and use of mixing system 10 will now be discussed. During assembly, mixing assembly 40 is coupled with container 18 as discussed above. The assembly can then be sterilized, such as by radiation, so that compartment 28 and the components therein are sterile. To facilitate shipping and storage, container 18 can be folded over at any location along the length of flexible tubular connector 42 so as to minimize the length and size of container assembly 16. During use, container assembly 16, including mixing assembly 40, is positioned within chamber 92 of support housing 14. Rotational assembly 48 is then removably connected to restrainer 136 of drive motor assembly 15 so that hub 54 is aligned with motor mount 118. Second end 170 of drive shaft 17 is advanced down through motor mount 118, through hub 54 of rotational assembly 48, through tubular connector 42 and finally into mixing element 64.

In this position, drive shaft 17 is locked to motor mount 118 with first driver portion 180 engaging hub 54 and second driver portion 178 engaging mixing element 64, as discussed above. As a result, rotation of motor mount 118 by drive motor 128 facilitates rotation of drive shaft 17 which in turn facilitates the concurrent rotation of hub 54, tubular connector 42, and mixing element 64. In turn, rotation of mixing element 64 facilities mixing and suspension of the liquid within compartment 28 of container 12.

A liquid, such as a cellular or microorganism culture, having a first volume can be disposed within compartment 28 of container 18. Mixing element 64, which is disposed at a first location within compartment 28 of container 18, can be moved, i.e., rotated, so as to mix the first volume of the liquid within compartment 28. Mixing element 64 can be moved by drive motor assembly 15 rotating drive shaft 17 on which mixing element 64 is attached. Liquid is added to compartment 28 of container 18 so as to form a second volume of liquid within compartment 28. Four bar linkage system 250 is used to raise mixing element 64 within compartment 28 of container 18 to a second position. This can be accomplished by four bar linkage system 250 raising drive motor assembly 15 which in turn raises drive shaft 17 and mixing element 64 attached thereto. Mixing element 64 is moved at the second position, such as by drive motor assembly 15 rotating drive shaft 17, so as to mix the second volume of liquid within the container. Four bar linkage system 250 can also simultaneously adjust the tilt or angular orientation of drive motor assembly 15, drive shaft 17 and/or mixing element 64 as mixing element 64 is raised from the first position to the second position so that mixing element 64 is at the desired lateral position within the container for mixing liquid at the second position.

In one embodiment, four bar linkage system 250 can be used to move the drive motor assembly 15, drive shaft 17 and/or mixing element 64 to a plurality of different fixed elevations as the level of liquid within container 18 changes, i.e., increases or decreases. For example, drive motor assembly 15, drive shaft 17 and/or mixing element 64 could each be moved to at least two, three, four, five, six or seven different elevations. Likewise, drive motor assembly 15, drive shaft 17 and/or mixing element 64 can each be simultaneously moved to a different tilt or angular orientation as they are each moved to a different elevation. In another alternative embodiment, a sensor, such as an optical sensor, can be used to monitor the height of the liquid within container 18. An electronic controller, such as computer or computer processor, can be electrically coupled with the sensor and four bar linkage system 250. The controller can then be used to automatically regulate the elevation and angular orientation of drive motor assembly 15, drive shaft 17 and/or mixing element 64 based on detected changes in the level of liquid within container 18.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A liquid mixing system comprising:
   a support housing at least partially bounding a chamber, the support housing having a top opening that communicates with the chamber;
   a mount secured to the support housing so as to span across the top opening; and
   a drive motor assembly secured to the mount by a four bar linkage system so that the drive motor assembly can be selectively raised and lowered between at least two positions, the four bar linkage system comprising four separate arms each having a first end hingedly connected to the drive motor assembly and an opposing second end hingedly connected to the mount, the drive motor assembly being configured to engage a drive shaft for moving the drive shaft within the chamber of the support housing.

2. The liquid mixing system as recited in claim 1, wherein the four bar linkage system is movable between a lowered position wherein the drive motor assembly is disposed at a first angular orientation and an elevated raised position wherein the drive motor assembly is disposed at a second angular orientation that is different from the first angular orientation.

3. The liquid mixing system as recited in claim 2, wherein an angular orientation of the drive motor assembly automatically changes as the four bar linkage system is moved between the lowered position and the raised position.

4. The liquid mixing system as recited in claim 1, wherein the mount comprises:
   an elongated first rail spanning across the top opening and having opposing ends secured to the support housing;
   an elongated second rail spanning across the top opening and having opposing ends secured to the support housing, the second rail being spaced apart from the first rail;
   a brace extending between the first rail and the second rail so as to be disposed over the top opening.

5. The liquid mixing system as recited in claim 4, wherein the first rail and the second rail are U-shaped or arch shaped and upwardly project from the support housing.

6. The liquid mixing system as recited in claim 1, further comprising a drive assembly that extends between the mount and the four bar linkage system and controls movement of the four bar linkage system.

7. The liquid mixing system as recited in claim 6, wherein the drive assembly comprises a hydraulic or pneumatic piston.

8. The liquid mixing system as recited in claim 1, wherein the support housing has an annular flange that encircles the top opening, the mount being secured on opposing sides of the annular flange so that the mount spans entirely across the top opening.

9. The liquid mixing system as recited in claim 1, further comprising a flexible bag disposed within the chamber of the support housing, the flexible bag bounding a compartment and being coupled to the drive motor assembly.

10. The liquid mixing system as recited in claim 9, further comprising a drive shaft coupled with the drive motor assembly, at least a portion of the drive shaft being disposed within the compartment of the flexible bag, the drive motor assembly rotating the drive shaft when the drive motor assembly is activated.

11. The liquid mixing system as recited in claim 10, further comprising a mixing element disposed within the compartment of the flexible bag and coupled with the drive shaft.

12. A liquid mixing system comprising:
   a support housing at least partially bounding a compartment;
   a mount secured to the support housing;
   a drive motor assembly configured to engage a drive shaft for moving the drive shaft within the compartment of the support housing; and
   a four bar linkage system extending between the mount and the drive motor assembly, the four bar linkage system being movable between a first position wherein the drive motor assembly is disposed at a first elevation and a second position wherein the drive motor assembly is disposed at a second elevation that is different from the first elevation, the four bar linkage system comprising four separate arms each having a first end hingedly connected to the drive motor assembly and an opposing second end hingedly connected to the mount.

13. The liquid mixing system as recited in claim 12, wherein the four bar linkage system automatically changes an angular orientation of the drive motor assembly as the drive motor assembly is moved from the first elevation to the second elevation.

14. The liquid mixing system as recited in claim 12, further comprising:
   a support extending between two of the four arms of the four bar linkage system; and
   a drive assembly extending between the mount and the support.

15. The liquid mixing system as recited in claim 14, wherein the drive assembly comprises a hydraulic or pneumatic piston.

16. A method for mixing a liquid, the method comprising:
   moving a mixing element disposed at a first location within a compartment of a container so as to mix a first volume of a liquid within the compartment;
   adding liquid to the compartment of the container so as to form a second volume of the liquid within the compartment;
   moving a four bar linkage system so as to raise the mixing element within the compartment of the container to a second position the four bar linkage system comprising four separate arms that are spaced apart, each of the four separate arms having a first end and an opposing second end that both hingedly pivot as the four bar linkage system moves to raise the mixing element; and moving the mixing element at the second position so as to mix the second volume of liquid within the container.

17. The method as recited in claim 16, wherein moving the mixing element comprises rotating the mixing element.

18. The method as recited in claim 16, wherein the step of moving the four bar linkage system automatically adjusts an angular orientation of the mixing element.

* * * * *